US010745371B2

(12) United States Patent
Giannousis et al.

(10) Patent No.: US 10,745,371 B2
(45) Date of Patent: Aug. 18, 2020

(54) METHODS FOR ENRICHING ALPHA-TOCOTRIENOL FROM MIXED TOCOL COMPOSITIONS

(71) Applicant: PTC Therapeutics, Inc., South Plainfield, NJ (US)

(72) Inventors: Peter Giannousis, Pacifica, CA (US); Paul Mollard, San Jose, CA (US); Noah M. Benjamin, San Francisco, CA (US); Jeffrey D. Butler, Rancho Cordova, CA (US); Olivier Dapremont, Rancho Cordova, CA (US); James B. Falabella, Rancho Cordova, CA (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 0 days.

(21) Appl. No.: 16/063,035

(22) PCT Filed: Dec. 16, 2016

(86) PCT No.: PCT/US2016/067377
§ 371 (c)(1),
(2) Date: Jun. 15, 2018

(87) PCT Pub. No.: WO2017/106786
PCT Pub. Date: Jun. 22, 2017

(65) Prior Publication Data
US 2018/0362492 A1 Dec. 20, 2018

Related U.S. Application Data

(60) Provisional application No. 62/386,943, filed on Dec. 16, 2015, provisional application No. 62/386,949, filed on Dec. 16, 2015.

(51) Int. Cl.
*C07D 311/72* (2006.01)
(52) U.S. Cl.
CPC .................. *C07D 311/72* (2013.01)
(58) Field of Classification Search
CPC ................................................ C07D 311/72
See application file for complete search history.

(56) References Cited

U.S. PATENT DOCUMENTS

| | | | |
|---|---|---|---|
| 2,519,863 A | 8/1950 | Weisler | |
| 4,603,142 A | 7/1986 | Burger et al. | |
| 4,977,282 A | 12/1990 | Baldwin et al. | |
| 5,157,132 A | 10/1992 | Tan et al. | |
| 5,190,618 A | 3/1993 | Top et al. | |
| 5,660,691 A | 8/1997 | Barnicki et al. | |
| 5,801,159 A | 9/1998 | Miller et al. | |
| 5,932,748 A | 8/1999 | Breuninger | |
| 6,066,731 A | 5/2000 | Müller et al. | |
| 6,224,717 B1 | 5/2001 | Sumner, Jr. et al. | |
| 6,232,060 B1 | 5/2001 | Miller et al. | |
| 6,239,171 B1 | 5/2001 | Lane et al. | |
| 6,252,071 B1 | 6/2001 | Müller et al. | |
| 6,271,420 B1 | 8/2001 | Lohr | |
| 6,359,132 B1 | 3/2002 | Müller et al. | |
| 6,395,915 B1 | 5/2002 | Bellafiore et al. | |
| 6,562,372 B1 | 5/2003 | Yokoi et al. | |
| 6,590,113 B1 | 7/2003 | Sleeter | |
| 6,608,196 B2 | 8/2003 | Wang et al. | |
| 6,653,346 B1 | 11/2003 | Wang et al. | |
| 6,656,358 B2 | 12/2003 | May et al. | |
| 6,838,104 B2 | 1/2005 | Jacobs | |
| 6,977,270 B2 | 12/2005 | Baldenius et al. | |
| 7,034,054 B2 | 4/2006 | Miller et al. | |
| 7,038,067 B2 | 5/2006 | Couladouros et al. | |
| 7,432,305 B2 | 10/2008 | Miller et al. | |
| 7,470,798 B2 | 12/2008 | Wang et al. | |
| 7,491,312 B2 | 2/2009 | Gilat et al. | |
| 7,514,461 B2 | 4/2009 | Wang et al. | |
| 7,968,746 B2 | 6/2011 | Jankowski et al. | |
| 8,314,153 B2 | 11/2012 | Miller et al. | |
| 8,575,369 B2 | 11/2013 | Wesson et al. | |
| 8,716,486 B2 | 5/2014 | Hinman et al. | |
| 8,716,527 B2 | 5/2014 | Hinman et al. | |
| 8,952,071 B2 | 2/2015 | Hinman et al. | |
| 9,162,957 B2 | 10/2015 | Mollard | |
| 9,278,085 B2 | 3/2016 | Miller et al. | |
| 9,296,712 B2 | 3/2016 | Hinman et al. | |
| 9,370,496 B2 | 6/2016 | Miller | |
| 2003/0176361 A1 | 9/2003 | Wang et al. | |
| 2004/0116715 A1 | 6/2004 | Baldenius et al. | |

(Continued)

FOREIGN PATENT DOCUMENTS

| | | | |
|---|---|---|---|
| JP | 63063674 A | 3/1988 | |
| JP | 1233278 A | 9/1989 | |

(Continued)

OTHER PUBLICATIONS

Written Opinion dated Dec. 23, 2009, for PCT Patent Application No. PCT/US09/62212, filed on Oct. 27, 2009, 6 pages.
Bertalan et al., "Recovery of fatty oil from theTransylvanian black current by means of supercritical and conventional extraction", Olaj, Szappn, Kozmetika, 2000, vol. 49 (Kulonszarriy), pp. 40-45; with English translation 14 pages.
Borch, R. F.,"Cyanohydridoborate anion as a selective reducing agent," Journal of the American Chemical Society 93, No. 12 (1971), pp. 2897-2904.
Cheremisinoff, N. P., Liquid filtration. Butterworth-Heinemann, 1998, pp. 1-18.

(Continued)

*Primary Examiner* — Timothy R Rozof
(74) *Attorney, Agent, or Firm* — Squire Patton Boggs (US) LLP

(57) ABSTRACT

Provided herein are methods for making an alpha-tocotrienol enriched tocol mixture, such as from a plant or plant-derived material. Also provided herein are simulated moving bed purification methods for tocotrienol compounds such as alpha tocotrienol.

21 Claims, 2 Drawing Sheets

(56) References Cited

U.S. PATENT DOCUMENTS

| | | |
|---|---|---|
| 2004/0158083 A1 | 8/2004 | Choo et al. |
| 2005/0124687 A1 | 6/2005 | Couladouros et al. |
| 2006/0051844 A1 | 3/2006 | Heavner et al. |
| 2006/0281809 A1 | 12/2006 | Miller et al. |
| 2007/0238886 A1 | 10/2007 | Ho |
| 2009/0076278 A1 | 3/2009 | Dan-Oh et al. |
| 2009/0291092 A1 | 11/2009 | Miller et al. |
| 2010/0010100 A1 | 1/2010 | Hinman et al. |
| 2010/0029706 A1 | 2/2010 | Miller et al. |
| 2010/0029784 A1 | 2/2010 | Hinman et al. |
| 2010/0056429 A1 | 3/2010 | Miller et al. |
| 2010/0105930 A1* | 4/2010 | Wesson ............... C07D 311/72 549/408 |
| 2010/0266591 A1 | 10/2010 | Bugelski et al. |
| 2011/0142834 A1 | 6/2011 | Miller |
| 2011/0207828 A1 | 8/2011 | Miller et al. |
| 2011/0263720 A1 | 10/2011 | Paisley et al. |
| 2011/0269776 A1 | 11/2011 | Miller |
| 2012/0101169 A1 | 4/2012 | Hawi |
| 2012/0122969 A1 | 5/2012 | Miller et al. |
| 2012/0136048 A1 | 5/2012 | Miller et al. |
| 2012/0295985 A1 | 11/2012 | Miller et al. |
| 2013/0109759 A1 | 5/2013 | Miller |
| 2013/0116336 A1 | 5/2013 | Shrader |
| 2013/0267538 A1 | 10/2013 | Walkinshaw et al. |
| 2013/0345312 A1 | 12/2013 | Jankowski et al. |
| 2014/0031433 A1 | 1/2014 | Miller et al. |
| 2014/0179933 A1 | 6/2014 | Oroskar et al. |
| 2014/0243424 A1 | 8/2014 | Mollard et al. |
| 2014/0249160 A1 | 9/2014 | Miller et al. |
| 2014/0256830 A1 | 9/2014 | Hinman et al. |
| 2014/0275045 A1 | 9/2014 | Hinman et al. |
| 2014/0343166 A1 | 11/2014 | Miller et al. |
| 2015/0057363 A1 | 2/2015 | Miller et al. |
| 2015/0216820 A1 | 8/2015 | Miller et al. |
| 2015/0218079 A1 | 8/2015 | Shrader et al. |
| 2015/0297551 A1 | 10/2015 | Hinman et al. |
| 2016/0024085 A1 | 1/2016 | Hinman et al. |
| 2016/0039775 A1 | 2/2016 | Hinman et al. |
| 2016/0039776 A1 | 2/2016 | Hinman et al. |
| 2016/0115141 A1 | 4/2016 | Hinman et al. |
| 2018/0000749 A1 | 1/2018 | Mollard et al. |
| 2018/0002247 A1 | 1/2018 | Mollard et al. |
| 2018/0362492 A1 | 12/2018 | Giannousis et al. |
| 2019/0029975 A1 | 1/2019 | Shrader |

FOREIGN PATENT DOCUMENTS

| | | |
|---|---|---|
| JP | 2003-2777 | 1/2003 |
| JP | 2003-171376 | 6/2003 |
| JP | 2004-175805 | 6/2004 |
| WO | WO 99/38860 | 8/1999 |
| WO | WO 2002/050054 A2 | 6/2002 |
| WO | WO 2007/105336 A1 | 9/2007 |
| WO | WO 2008/142433 A1 | 11/2008 |
| WO | WO 2011/113018 | 9/2011 |
| WO | WO 2012/154613 | 11/2012 |
| WO | WO 2013/006736 | 1/2013 |
| WO | WO 2012/170773 | 12/2013 |
| WO | WO 2016/114860 | 7/2016 |
| WO | WO 2017/106803 | 6/2017 |
| WO | WO 2017/123823 | 6/2017 |
| WO | WO 2018/081644 A1 | 5/2018 |
| WO | WO 2018/093957 A1 | 5/2018 |
| WO | WO 2018/129411 A1 | 7/2018 |
| WO | WO 2018/191732 A1 | 10/2018 |

OTHER PUBLICATIONS

Gu et al., "5-Trideuteromethyl-α-tocotrienol and 5-$^{14}$CH$_3$-α-tocotrienol as biological tracers of tocotrienols", *Journal of Labelled Compounds and Radiopharmaceuticals*, 2006, vol. 49, pp. 733-743.

International Search Report dated Dec. 23, 2009, for PCT Patent Application No. PCT/US09/62212, filed on Oct. 27, 2009, 2 pages.

Kabbe et al., "A new synthesis of 3,4-dehydro-a-tocotrienol and vitamin E", *Synthesis*, 1978, vol. 12, pp. 888-889. (Translation of Abstract only: Chemical Abstract CAPLUS No. 1979:168774, 2 pages).

Kajiwara et al., "Studies on Tocopherols 111. Convenient Synthesis of Tocopherols," Heterocycles, 1980, vol. 14, No. 12, pp. 1995-1998.

Maeda, Y. et al. (Dec. 16, 1994). "Rearrangement of (Polymethoxybenzyl) Ammonium N-Methylides," J. Org. Chem. 59(25):7897-7901.

Mayer, H. et al. (1967). "Ober die Chemie des Vitamins E. 8. Mitteilung [1]. Die Stereochemie von natulichem y-Tocotrienol (Plastochromanol-3), Plastochromanol-8 and Plastochromenol-81)," Helvetica Chimica Acta 50(5):1376-1393. (Translation of Abstract Only: Chemical Abstracts CAPLUS Abstract No. 1967:473698. 1 page, and publisher's document Web page description, 2 pages.).

Netscher et al. (2007). "Tocopherols by Hydride Reduction of Dialkylamino Derivatives," European Journal of Organic Chemistry, pp. 1176-1183.

Netscher et al. (Sep. 2001). "Aminomethylation of Vitamin E Compounds," located at <http://www.mdpi.net/ecsoc/ecsoc-5/Papers/c0007/c0007.htm, last visited on Oct. 21, 2008, 4 pages.

Ogawa et al., "γ-Tocopheryl Quinone, Not A-Tocopheryl Quinone, Induces Adaptive Response Through Up-Regulation of Cellular Glutathione and Cysteine Availability Via Activation of ATF4", *Free Radical Research*, Jul. 2008, vol. 42, No. 7, pp. 674-687.

Pearce et al., "Inhibitors of Cholesterol Biosynthesis. 2. Hypocholesterolemic and Antioxidant Activities of Ben zopyran and Tetrahydronaphthalene Analogues of the Toeotrienols", *J. Med. Chem.*, 1994, vol. 37, pp. 526-541.

Pearce et al. "Hypocholesterolemic Activity of Synthetic and Natural Tocotrienols", *J. Med. Chem.*, 1992, vol. 35, pp. 3595-3606.

Schudel et al., "Uber die Chemie des Vitamins E. 5. Mitteilung. Die Synthese von rac. all-trans-ξ$_1$-and-ε-Tocopherol," *Helvetica Chimica Acta*, 1963, vol. XLVI, Fasc. 7, No. 281, pp. 2517-2526. (English summary on p. 2526.).

Scott et al., "Syntheses of (2R,4'R,8'R)-α-Tocopherol and (2R,3'E,7'E)-α-Tocotrienol," *Helvetica Chimica Acta*, 1976, vol. 59, Fasc. 1, pp. 290-306, Nr. 34-35.

Strohschein et al., "Separation and Identification of Tocotrienol Isomers by HPLC-MS and HPLC-NMR Coupling," *Anal Chem*, 1999, vol. 71, pp. 1780-1785.

Tayama et al. (2006). "Asymmetric [1,2] Stevens Rearrangement of (S)-N-Benzylic Proline-Derived Ammonium Salts under Biphasic Conditions," Chemistry Letters 35(5):478-479.

Urano et al., "Synthesis of dl-α-Tocopherol and dl-α-Tocotrienol", *Chem. Pharm. Bull.*, 1983, vol. 31, pp. 4341-4345.

Wu et al. (2007). "Preparation of High Content d-a-tocopherol," China Oils and Fats (Zhongguo Youzhi) 32(6):55-57; (English abstract only).

International Search Report and Written Opinion of PCT/US2016/067377 dated May 9, 2017, 18 pages.

Thornton, D. E., "Antioxidant and cytotoxic tocopheryl quinones in normal and cancer cells." Free Radical Biology and Medicine 18.6 (1995):963-976.

* cited by examiner

METHODS FOR ENRICHING ALPHA-TOCOTRIENOL FROM MIXED TOCOL COMPOSITIONS

CROSS-REFERENCE TO RELATED APPLICATIONS

This application is a filing under 35 U.S.C. § 371 of International Patent Application No. PCT/US2016/067377, filed Dec. 16, 2016, which claims the benefit of U.S. Provisional Patent Application No. 62/386,943, filed Dec. 16, 2015, and of U.S. Provisional Patent Application No. 62/386,949, filed Dec. 16, 2015. Each of the foregoing applications is incorporated herein by reference in its entirety.

FIELD

Provided herein are methods for making an alpha-tocotrienol enriched tocol mixture, such as from a plant or plant-derived material. Also provided herein are simulated moving bed purification methods for tocotrienol compounds such as alpha tocotrienol.

BACKGROUND

Certain plants contain mixtures of tocol compounds, such as tocopherol (alpha, beta, gamma and/or delta tocopherols) and/or tocotrienol (alpha, beta, gamma and/or delta tocotrienols) compounds. Previous methods have been used to obtain alpha-tocotrienol containing compositions from natural plant sources, such as palm oils and refined palm oils. Some processes for producing alpha-tocotrienol from plant sources produce alpha-tocotrienol by alkylating beta-, gamma-, and delta-tocotrienols; however, those processes result in a lower amount of alpha-tocotrienol than might otherwise be obtained. In particular, it has been difficult to obtain desirable amounts of alpha-tocotrienol from plant sources containing more than about 5% phytosterol content.

What is needed are improved methods for enriching alpha-tocotrienol from natural plant sources. Furthermore, what is needed are methods for enriching alpha-tocotrienol from natural plant sources, wherein higher amounts of alpha-tocotrienol may be obtained by converting the beta-, gamma-, and delta-tocotrienols to alpha-tocotrienol. The methods provided herein are capable of solving this and other problems.

SUMMARY

In one aspect is a method of making an alpha-tocotrienol enriched tocol mixture. In some embodiments, the method includes (a) contacting a tocol mixture with an amino-alkylating agent, wherein the tocol mixture comprises at least one non-alpha tocotrienol, at least one non-tocol, optionally alpha tocotrienol, and optionally one or more tocopherols, whereby the at least one non-alpha tocotrienol is amino-alkylated; (b) reducing the amino-alkylated non-alpha tocotrienols to alpha tocotrienol with a reducing agent; (c) removing one or more waxy impurities from the mixture; (d) contacting the mixture with an agent that binds one or more polar impurities; and (e) removing the agent. In some embodiments, the method further includes after step (c): (c)(1) converting the alpha-tocotrienol to an alpha-tocotrienol salt; (c)(2) providing a polar solvent phase and a non-polar solvent phase and partitioning the alpha-tocotrienol salt to the polar solvent phase; (c)(3) removing the non-polar solvent phase; and (c)(4) converting the alpha-tocotrienol salt in the polar solvent phase to alpha-tocotrienol. In some embodiments, including any of the foregoing embodiments, the method further includes after step (a): (a)(1) removing water formed from the reaction of step (a).

In some embodiments, the alpha-tocotrienol in step (c)(1) is converted to the alpha tocotrienol salt with an inorganic salt base having a $pK_a$ of more than about 10. In some embodiments, the inorganic salt base is sodium methoxide (NaOMe).

In some embodiments, the polar solvent phase in step (c)(2) contains N-methyl-pyrrolidone (NMP). In some embodiments, the non-polar solvent phase in step (c)(2) contains an alkane. In some embodiments, the non-polar solvent phase in step (c)(2) contains a hexane or a heptane. In some embodiments, the non-polar solvent phase in step (c)(2) contains n-heptane.

In some embodiments, the partitioning between the polar and non-polar solvent phases in step (c)(2) is performed at less than 10° C. In some embodiments, the partitioning between the polar and non-polar solvent phases in step (c)(2) is performed at about 0° C.

In some embodiments, converting the alpha tocotrienol salt to alpha tocotrienol in step (c)(4) includes addition of an acid having a pKa of less than about 7. In some embodiments, converting the alpha tocotrienol salt to alpha tocotrienol in step (c)(4) includes addition of HCl.

In some embodiments, step (c)(4) includes production of a salt by-product, and the method further includes a step (c)(5) after step (c)(4), wherein step (c)(5) includes removing the salt by-product produced in step (c)(4). In some embodiments, step (c)(5) comprises solvent extraction with a non-polar light phase, followed by retaining the non-polar light phase. In some embodiments, the non-polar light phase comprises toluene, a heptane or a combination thereof. In some embodiments, the heptane is n-heptane. In some embodiments, the non-polar light phase is washed with an aqueous wash.

In some embodiments, step (a)(1) includes an azeotropic distillation to remove the water. In some embodiments, step (a)(1) includes an azeotropic distillation in the presence of a solvent with a boiling point of at least 80° C. at 1 atm pressure. In some embodiments, step (a)(1) includes an azeotropic distillation in the presence of a solvent with a boiling point of at least 95° C. at 1 atm pressure. In some embodiments, the solvent is selected from the group consisting of: 2-butanol, 2-pentanol, 2-methyl-2-butanol, ethanol, toluene, ethanol, toluene, ethyl acetate, acetonitrile, methyl ethyl ketone, cyclohexanol, 2-pentanol, 2-hexanol, and 2-methyl-1-propanol. In some embodiments, the solvent is 2-methyl-2-butanol.

In some embodiments, the amino-alkylating agent in step (a) includes a secondary amine and a formaldehyde equivalent. In some embodiments, the secondary amine is N-methyl-piperazine. In some embodiments, the formaldehyde equivalent is paraformaldehyde.

In some embodiments, the reducing agent in step (b) is a borohydride. In some embodiments, the reducing agent in step (b) is $NaBH_3CN$. In some embodiments, an alcohol having a boiling point of at least about 95° C. is used as a solvent in step (b). In some embodiments, the solvent in step (b) is a four or five carbon alcohol. In some embodiments, the solvent in step (b) is 2-methyl-2-butanol.

In some embodiments, wherein one or more byproducts are produced in steps (a) and/or (b), and wherein the mixture optionally contains residual secondary amine, the method includes a step (b)(1) after step (b), wherein step (b)(1)

includes removing at least one of the one or more byproducts produced in steps (a) and/or (b) and removing the optional residual secondary amine. In some embodiments, step (b)(1) includes an aqueous work up. In some embodiments, the aqueous work up includes (i) contacting the mixture with isopropyl acetate and water, whereby an aqueous phase is formed; (ii) removing the aqueous phase; and (iii) performing an acid wash on the mixture. In some embodiments, step (i) of the aqueous work up includes contacting the mixture with isopropyl acetate, water, and $Na_2HPO_4$, whereby an aqueous phase is formed. In some embodiments, the aqueous work up comprises (i) contacting the mixture with isopropyl acetate and water, whereby an aqueous phase is formed; (ii) removing the aqueous phase; (iii) contacting the mixture with water, whereby an aqueous phase is formed, and removing the aqueous phase, and (iv) performing an acid wash on the mixture.

In some embodiments, step (c) includes cooling and/or removing solvent that may be present in the mixture to precipitate the one or more waxy impurities. In some embodiments, the cooling in step (c) includes cooling to about −35° C. to about 5° C. In some embodiments, the cooling in step (c) includes cooling to about −20° C. to about −10° C. In some embodiments, the cooling in step (c) comprises cooling to about −35° C. to about −15° C.

In some embodiments, removing the one or more waxy impurities in step (c) includes contacting the mixture and a solid binding material. In some embodiments, wherein removing the one or more waxy impurities comprises contacting the mixture with the solid binding material to produce a slurry, followed by filtering the slurry and retaining the filtrate. In some embodiments, the solid binding material is a finely divided solid comprising carbon, silica, alumina, or diatomaceous earth. In some embodiments, the solid binding material is Celite®.

In some embodiments, step (c) includes addition of heptane and holding the mixture at a temperature of about 20° C. to 30° C. In some embodiments, the mixture is held at a temperature of about 20° C. to 30° C. for from about 1 to about 4 hours. In some embodiments, step (c) further includes filtering the mixture to remove insoluble solid by-products. In some embodiments, step (c) includes an aqueous work up. In some embodiments, the aqueous work up comprises (i) contacting the mixture with water, whereby an aqueous phase is formed, and removing the aqueous phase, and (ii) performing an acid wash on the mixture. In some embodiments, the acid wash comprises citric acid.

In some embodiments, step (c) includes reducing the mixture to about a minimum stir volume. In some embodiments, the mixture is reduced to a minimum stir volume by distillation in the presence of a solvent. In some embodiments, the solvent is heptane, t-AmOH, or a combination thereof.

In some embodiments, the agent in step (d) comprises silica, Celite®, Diatomaceous earth, alumina, or florisil. In some embodiments, steps (d) and (e) comprise adding the mixture to a column comprising the agent, and eluting the mixture off the column.

In some embodiments, the method further includes after step (e): (f) solvent exchange of the mixture to a solvent selected from the group consisting of methanol and acetonitrile. In some embodiments, the solvent exchange is to methanol. In some embodiments, the solvent exchange is to acetonitrile. In some embodiments, the solvent exchange is carried out in the absence of light.

In some embodiments, the tocol mixture in step (a) is a palm oil or a material derived from palm oil. In some embodiments, the tocol mixture is Tocomin 50®. In some embodiments, the phytosterol content of the tocol mixture is at least about 5%, at least about 7%, at least about 8%, at least about 10%, or at least about 12%. In some embodiments, the tocol mixture in step (a) comprises at least about 65 (A) % tocols, at least about 68 (A) % tocols, or at least about 70 (A) % tocols. In some embodiments, the tocol mixture is Gold Tri.E™ 70. In some embodiments, the tocol mixture comprises 84 (A) % of a mixture of tocotrienols and tocopherols.

In some embodiments, the product of the method has a content of at least about 50 wt % alpha-tocotrienol, at least about 55 wt. % alpha-tocotrienol, or at least about 58 wt % alpha-tocotrienol.

In another aspect is a method of purifying a tocotrienol feed solution, comprising passing the feed solution through a chromatographic process. In some embodiments, the chromatographic process is a simulated moving bed (SMB) apparatus. In some embodiments, the method includes: (a) passing the feed solution through a chromatographic process comprising a stationary phase and a mobile phase stream, wherein said feed solution comprises the tocotrienol and one or more impurity compounds; (b) operating the chromatographic process as a simulated moving bed (SMB) process under conditions effective to purify the tocotrienol from at least one impurity compound; (c) collecting a stream from the SMB apparatus, wherein said stream comprises the purified tocotrienol; and (d) optionally repeating steps (a)-(c).

In some embodiments, the chromatographic process is a continuous chromatographic process. In some embodiments, the chromatographic process is a semi-continuous chromatographic process.

In some embodiments, the stream containing the purified tocotrienol is the extract stream. In some embodiments, the stream containing the purified tocotrienol is the raffinate stream.

In some embodiments, the stream containing the purified tocotrienol is the extract stream in a first pass, and wherein the stream containing the purified tocotrienol is the raffinate stream in a second or subsequent pass. In some embodiments, the stream containing the purified tocotrienol is the raffinate stream in a first pass, and wherein the stream containing the purified tocotrienol is the extract stream in a second or subsequent pass.

In some embodiments, the tocotrienol that is purified is selected from the group consisting of alpha-tocotrienol, beta-tocotrienol, delta-tocotrienol, and-gamma tocotrienol. In some embodiments, the tocotrienol that is purified is alpha-tocotrienol.

In some embodiments, the stationary phase is selected from the group consisting of silica gel, functionalized silica gel, reverse phase gel, or chiral phase gel. In some embodiments, the stationary phase has a particle size of about 2 to about 300 μm, about 5 to about 50 μm, or about 20 to about 30 μm.

In some embodiments, the mobile phase stream includes one or more solvents selected from the group consisting of: water, acetonitrile, t-AmOH, methanol, ethanol, n-proposal, isopropyl alcohol, butanol, ethyl acetate, isopropyl acetate, MtBE, diethyl ether, fluorinated solvents, alkanes, hexanes, n-hexane, heptanes, n-heptane, methyl-cyclopentane, pentane, methyl-cyclohexane, cyclohexane, Toluene, and $CO_2$. In some embodiments, the mobile phase stream contains acetonitrile. In some embodiments, the mobile phase stream contains methanol.

In some embodiments, the tocotrienol feed solution is obtained using a method of making an alpha-tocotrienol enriched tocol mixture as disclosed herein.

In some embodiments, the a final product stream containing purified tocotrienol contains the tocotrienol with at least about 90 (A) % purity. In some embodiments, the final product stream containing purified tocotrienol is concentrated to a tocotrienol concentration of at least about 90 wt %.

In some embodiments, the chromatographic process includes 2 to 30 columns serially connected, 2 to 12 columns serially connected, or 5 to 8 columns serially connected.

In some embodiments, the chromatographic process is operated at a rate of about 0.05 to about 5 kg feed stream per kg stationary phase per 24 hours, or about 1 to about 3 kg feed stream per kg stationary phase per 24 hours. In some embodiments, the chromatographic process is operated at a pressure of about 2 bar to about 100 bar, about 5 bar to about 60 bar, 20 bar to about 45 bar, or about 30 bar to about 45 bar pressure. In some embodiments, the chromatographic process is operated at a temperature of about 10° C. to about 50° C., about 15° C. to about 40° C., about 20° C. to about 35° C., or about 25° C. to about 30° C.

In some embodiments, the extract stream is collected and tocotrienol containing fractions are subjected to a method of making an alpha-tocotrienol enriched tocol mixture as disclosed herein. In some embodiments, the extract stream which is subjected a method of making an alpha-tocotrienol enriched tocol mixture as disclosed herein is then purified according to a method of purifying a tocotrienol feed solution as disclosed herein.

In some embodiments, the raffinate stream is collected and tocotrienol containing fractions are subjected to a method of making an alpha-tocotrienol enriched tocol mixture as disclosed herein. In some embodiments, the raffinate stream which is subjected a method of making an alpha-tocotrienol enriched tocol mixture as disclosed herein is then purified according to a method of purifying a tocotrienol feed solution as disclosed herein.

In another aspect of the invention is a composition comprising alpha-tocotrienol, produced by a method as described herein.

DESCRIPTION OF EXEMPLARY EMBODIMENTS

Definitions

Figure 1:
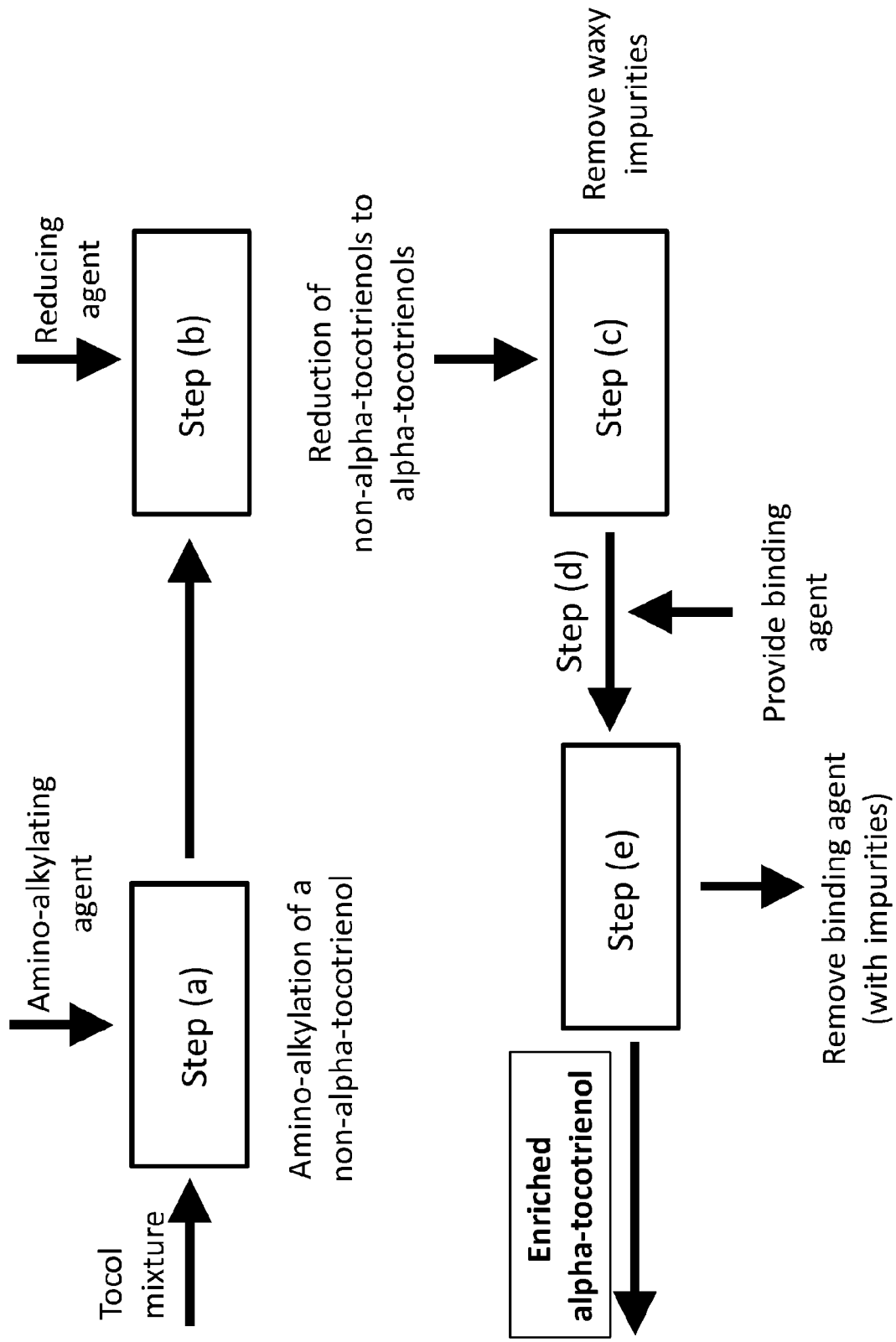
FIG. 1 provides a schematic of an exemplary embodiment of a method of making an alpha-tocotrienol enriched tocol mixture as disclosed herein.
Figure 2:
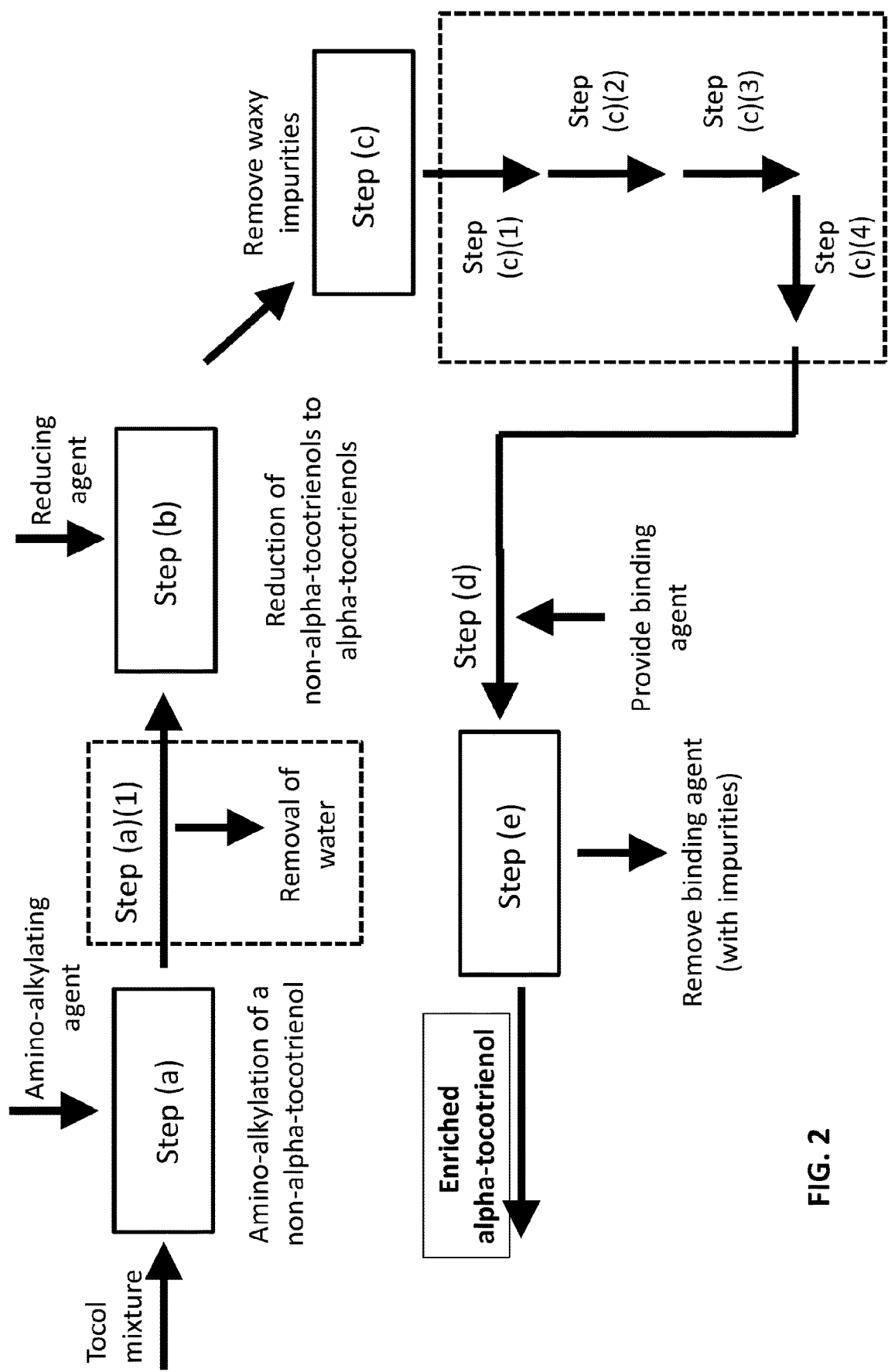
FIG. 2 provides a schematic of an exemplary embodiment of a method of making an alpha-tocotrienol enriched tocol mixture as disclosed herein. Dotted lines indicates steps that are optional, depending on the amount of tocotrienol or alpha-tocotrienol in the initial starting material.

It is to be understood that the description of methods and compositions described herein include "comprising", "consisting of", and "consisting essentially of" embodiments. For example, when a method is described as "consisting essentially of" the listed steps, the method contains the steps listed, and may contain other steps that do not substantially affect the method for producing the alpha-tocotrienol enriched compositions, but the method does not contain any other steps which substantially affect the method other than those steps expressly listed.

Reference to "about" a value or parameter herein includes (and describes) variations that are directed to that value or parameter per se. For example, description referring to "about X" includes description of "X".

As used herein, and unless otherwise specified, the terms "about" and "approximately," when used in connection with e.g. temperatures, concentration, amounts, size, pK, pH, or weight percent, mean a temperature, concentration, amount, size, pK, pH, or weight percent that is recognized by those of ordinary skill in the art to provide an equivalent effect to that obtained from the specified temperature, concentration, amount, size, pK, pH, or weight percent. Specifically, the terms "about" and "approximately," when used in this context, contemplate a temperature, concentration, amount, size, pK, pH, or weight percent within 15%, within 10%, within 5%, within 4%, within 3%, within 2%, within 1%, or within 0.5% of the specified temperature, concentration, amount, size, pK, pH, or weight percent.

The terms "a" or "an," as used in herein means one or more, unless context clearly dictates otherwise.

"Amino-alkylating agent" as used herein means an agent capable of adding an amino-alkyl group to a tocotrienol. For example, an amino-alkylating agent can include a secondary amine and a formaldehyde equivalent, wherein the secondary amine and formaldehyde equivalent are as disclosed herein.

"Tocol" indicates tocopherols and/or tocotrienols, in some embodiments alpha-tocopherol, beta-tocopherol, gamma-tocopherol, delta-tocopherol, alpha-tocotrienol, beta-tocotrienol, gamma-tocotrienol, and/or delta-tocotrienol. This includes all stereoisomers of the tocotrienol and tocopherol compounds, including, for example, diastereomers and enantiomers. The term "tocol" also includes mixtures of tocopherol and/or tocotrienol stereoisomers in any ratio, including, but not limited to, racemic mixtures, and their use in the methods. Unless stereochemistry is explicitly indicated in a structure, the structure is intended to embrace all possible stereoisomers of the compound depicted. If stereochemistry is explicitly indicated for one portion or portions of a molecule, but not for another portion or portions of a molecule, the structure is intended to embrace all possible stereoisomers for the portion or portions where stereochemistry is not explicitly indicated. The structures of exemplary tocopherols and tocotrienols is provided in Table 1 below:

TABLE 1
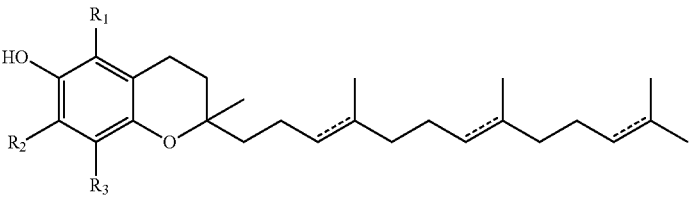

TABLE 1-continued

| | R₁ | R₂ | R₃ |
|---|---|---|---|
| Delta-tocopherol | H | H | methyl |

In some embodiments, exemplary tocopherols and tocotrienols contemplated for use in the methods disclosed herein have the structures as provided in Table 2 below:

TABLE 2

Alpha-tocotrienol

Beta-tocotrienol

Gamma-tocotrienol

Delta-tocotrienol

Alpha-tocopherol

TABLE 2-continued

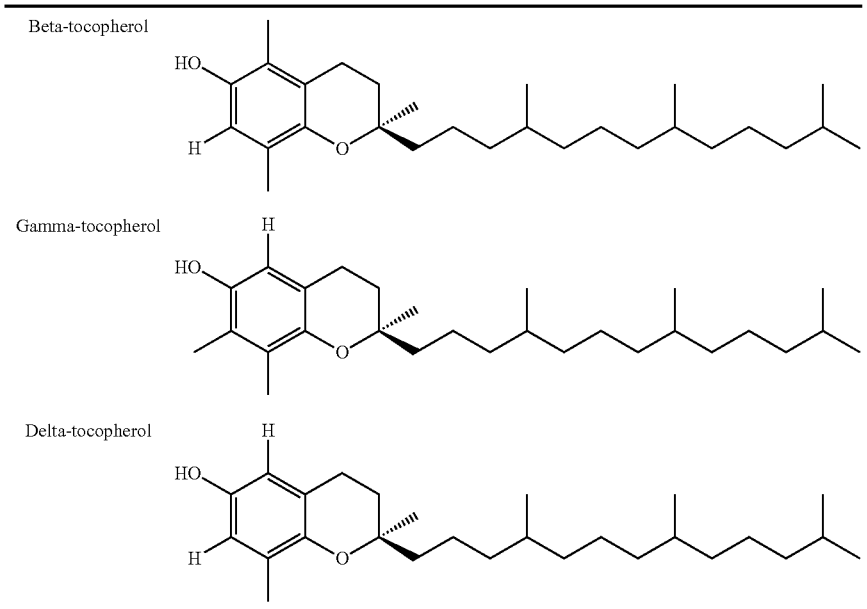

A "tocol mixture" comprises at least one tocol (e.g. one, two, three, four, or more tocols). In certain embodiments, including any of the foregoing embodiments, the tocol mixture is derived from a plant material. In certain embodiments, including any of the foregoing embodiments, the tocol mixture is derived from palm oil, a palm fruit extract, or a mixture of palm oil and palm fruit extract. In some embodiments, the tocol mixture is derived from palm oil. In some embodiments, the tocol mixture is a commercially available product comprising an enriched tocotrienol extract derived from palm oil. For example, the commercially available product can be one or more products as provided by Carotech, Golden Hope Bioorganic, Davos Life Science, Beijing Gingko Group, Eisai, Eastman Corporation, Oryza Oil & Fat Company, Sime Darby Biorganic Sdn Bhd or Palm Nutraceuticals. These commercially available products include, but are not limited to, Nu Triene Tocotrienol® (30% content, a product of Eastman Chemical Company); various Oryza® tocotrienol products of different tocotrienol concentrations from Oryza Oil & Fat Co. Ltd, including Oryza tocotrienol-70 with 70% total tocopherol/tocotrienol content, and a total tocotrienol content of 40% including 14% of alpha-tocotrienol and 24% gamma-tocotrienol, and Oryza tocotrienol-90 with 90% total tocopherol/tocotrienol content and a total tocotrienol content of 60%; Golden Hope Plantations Berhad Tocotrienol oil (70% content), Davos Life Science TRF (63% content), Davos Life Science TC84 (84% content); Ginnoway tocotrienol concentrate from palm and rice oil from Beijing Gingko Group, Gold Tri.E™, a product of Sime Darby Biorganic Sdn Bhd and Palm Nutraceuticals Sdn Bhd (89% content). Delta Tocotrienol-92® (92% pure by HPLC) is a commercially available product from Beijing Gingko Group that may be also used in the methods disclosed herein. In certain embodiments, the tocol mixture is a Tocomin® product, for example, Tocomin 50®. In some embodiments, the tocol mixture is Gold Tri.E™ 70. In some embodiments, the tocol mixture is natural palm oil, e.g., TC84 (Davos Life Science).

"Non-tocol" indicates an organic compound other than a tocol. In certain embodiments, including any of the foregoing embodiments, the non-tocol is selected from the group consisting of sterols, tocomonoenols, tocodienols, squalene, carotenoids, and glycerate esters.

"Solvent exchange" indicates replacing a solvent (or solvent mixture) with a different solvent (or solvent mixture). In certain embodiments, including any of the foregoing embodiments, the original solvent is removed by vacuum distillation. In certain embodiments, including any of the foregoing embodiments, less than about 10% of the original solvent remains after solvent exchange. In certain embodiments, including any of the foregoing embodiments, less than about 9% of the original solvent remains after solvent exchange. In certain embodiments, including any of the foregoing embodiments, less than about 8% of the original solvent remains after solvent exchange. In certain embodiments, including any of the foregoing embodiments, less than about 7% of the original solvent remains after solvent exchange. In certain embodiments, including any of the foregoing embodiments, less than about 6% of the original solvent remains after solvent exchange. In certain embodiments, including any of the foregoing embodiments, less than about 5% of the original solvent remains after solvent exchange. In certain embodiments, including any of the foregoing embodiments, less than about 4% of the original solvent remains after solvent exchange. In certain embodiments, including any of the foregoing embodiments, less than about 3% of the original solvent remains after solvent exchange. In certain embodiments, including any of the foregoing embodiments, less than about 2% of the original solvent remains after solvent exchange. In certain embodiments, including any of the foregoing embodiments, less than about 1% of the original solvent remains after solvent exchange.

"Minimum stir volume" indicates the minimum volume of liquid needed in the reactor so that the stirring mechanism effectively stirs the reactor contents. For example, minimum stir volume can indicate about 5%, 10%, 15%, 20%, 25%, 30%, 35%, 40%, 50%, 55%, 60%, 65%, 70%, or 75% of the volume capacity of the reactor.

"Waxy impurities" indicates one or more undesired organic compounds each having a melting temperature of at least about 25° C. In some embodiments, the undesired organic compounds contain one or more hydrocarbon tails that are at least $C_{20}$ in length. In some embodiments, the undesired organic compounds contain one or more hydrocarbon tails that are at least $C_{22}$ in length. In some embodiments, the undesired organic compounds contain one or more hydrocarbon tails that are at least $C_{24}$ in length. In some embodiments, the undesired organic compounds contain one or more hydrocarbon tails that are at least $C_{26}$ in length. In some embodiments, the undesired organic compounds contain one or more hydrocarbon tails that are at least $C_{28}$ in length. In some embodiments, the undesired organic compounds contain one or more hydrocarbon tails that are at least $C_{30}$ in length. Waxy impurities can include, for example, squalene and other high molecular weight isoprene compounds having a melting temperature of at least about 25° C., at least about 28° C., or at least about 30° C.

"Polar impurities" indicates one or more undesired compounds that are more polar than the desired alpha-tocotrienol.

"Non-polar impurities" indicates one or more undesired compounds that are less polar than the desired alpha-tocotrienol.

"Polar solvent" indicates a solvent with significant bond polarizations, typically solvents with heteroatoms, such as ethyl acetate, methanol, acetonitrile. In another embodiment, a polar solvent is a solvent with a dielectric constant of greater than 15. The skilled practitioner would recognize whether a particular solvent is classified as polar. In some embodiments, a polar solvent is one or more solvents selected from the group consisting of: tetrahydrofuran (THF), ethyl acetate (EA), acetonitrile, dimethylformamide (DMF), dimethyl sulfoxide (DMSO), water, ethanol, methanol, and isopropanol. The skilled practitioner would contemplate other polar solvents which could be used herein. A polar protic solvent is one in which a hydrogen atom is bound to an oxygen or to a nitrogen.

"Non-polar solvent" indicates a solvent with very low or no bond polarizations, typically hydrocarbon solvents, such as heptane. In another embodiment, a solvent with a dielectric constant of less than 15. The skilled practitioner would recognize whether a particular solvent is classified as non-polar. In some embodiments, a non-polar solvent is one or more solvents selected from the group consisting of: dichloromethane, toluene, benzene, 1,4-dioxane, hexane, diethyl ether. The skilled practitioner would contemplate other nonpolar solvents which could be used herein.

"Non-polar light phase" indicates a non-polar solvent with a density less than the corresponding aqueous phase.

"Solid binding material" indicates a solid substance that is able to bind one or more compounds of interest under the reaction or purification conditions of interest. For example, a solid binding material may be used to bind one or more waxy impurities, and the waxy impurities removed from the desired material by removal of the solid binding material. In certain embodiments, including any of the foregoing embodiments, the solid binding material is a finely divided solid. In certain embodiments, including any of the foregoing embodiments, the finely divided solid comprises particles having an average size of about 60 microns or less. In certain embodiments, including any of the foregoing embodiments, the solid binding material comprises carbon, silica, alumina, or diatomaceous earth. In some embodiments, the solid binding material comprises finely divided carbon, silica, alumina, or diatomaceous earth.

"Aqueous work up" indicates one or more of: quenching a reaction to deactivate any unreacted reagents using, in some embodiments, an aqueous solution; cooling the reaction mixture or adding an antisolvent (including an aqueous solution) to induce precipitation, and collecting or removing the solids by filtration, decantation, or centrifugation; and separating the reaction mixture into organic and aqueous layers by liquid-liquid extraction.

"Inorganic salt base" refers to a salt of a base, wherein the counterion is inorganic. In certain embodiments, including any of the foregoing embodiments, the inorganic salt base is sodium methoxide (NaOMe), lithium methoxide (LiOMe), potassium methoxide (KOMe), or magnesium methoxide $(Mg(OMe)_2)$. In certain embodiments, including any of the foregoing embodiments, the inorganic salt base is NaOMe.

The term "simulated moving bed apparatus" or "SMB apparatus" is used herein to denote a continuous or semi continuous chromatographic process composed of a combination of columns, inlet and outlet valve manifolds, sources of feed stream and of eluent, and mechanism for the timed switching of flows through the inlet and outlet manifolds, by way of which simulated moving bed chromatography is practiced. A typical SMB system comprises a plurality of columns serially connected, each column having an inlet manifold arranged to direct incoming flow from a plurality of inlet lines to the column and an outlet manifold arranged to direct flow emerging from the column to a plurality of discharge lines; a source of a feed stream (also referred to as a "feed solution") comprising the species to be separated; an eluent source; and a controller for inlet and outlet valve manifolds that forms flow paths communicating each column with a selected inlet line and a selected discharge line, and for changing the inlet and discharge lines so selected at preselected time intervals.

A single manifold can serve as both the outlet manifold of one column and the inlet manifold of another. In certain embodiments, including any of the foregoing embodiments, the inlet manifold associated with each column joins the column with at least three, and preferably only three, inlet lines, while the outlet manifold associated with each column likewise joins the column with at least three, and preferably only three, discharge lines. Selections among the various lines in each manifold are achieved by conventional means, such as a remotely controlled on-off valve on each line or a remotely controlled multi-way valve. In certain embodiments, including any of the foregoing embodiments, feeds and withdrawals are performed simultaneously as follows: (i) eluent is fed at an inlet manifold at the upstream end, (ii) extract is withdrawn at an outlet manifold between the upstream end and the downstream end, (iii) the feed stream of species to be separated is fed through an inlet manifold between the extract withdrawal site and the downstream end, and (iv) raffinate is withdrawn through an outlet manifold at the downstream end.

After a selected time interval (referred to as the "switch time" of the system), the valve positions in the inlet and outlet manifolds are reconfigured to advance feed and withdrawal sites, in a common direction around the circuit, which is the same direction as the eluent flow. The new configuration is maintained for another selected time interval, which can either be of the same duration as the first or of a different duration, and the various sites of feeding and withdrawal, are advanced again. These incremental advancements are continued as feed solution continues to be supplied to the system, and the result is a simulated continuous-flow system. The pattern of introduction and withdrawal thus rotates around the column circuit.

The terms "extract" and "raffinate" are used herein as they are in conventional SMB terminology. Thus, "extract" denotes a fraction of the initial liquid mixture that contains the component(s) that is/are more strongly retained on the solid phase relative to the other component(s) and that elute(s) in a relatively purified form, i.e., relatively isolated from the less strongly retained component(s). The term "raffinate" denotes a fraction of the initial liquid mixture that contains the components(s) that is/are retained relatively weakly on the solid phase and that elute(s) in a relatively purified form, i.e., relatively isolated from the strongly retained component(s).

The expression "serially connected in a circuit" in reference to the various columns in the SMB apparatus denotes that the columns are joined by fluid transfer conduits through inlet and outlet manifolds that can be arranged to cause the discharge from each column to be fed to an adjacent column in the series in a loop.

Variations that have been developed in the prior SMB processes of the prior art can be applied in an analogous manner to the process of the present invention. Thus, in the various changes of functions of the multifunctional ports, the isolation points separating the two groups of columns and all introduction and withdrawal sites can be advanced either simultaneously or in an asynchronous or staged manner (as in the Varicol variation, U.S. Pat. Nos. 6,136,198, 6,375,839, 6,413,419, and 6,712,973) or at variable flow rates (as in the PowerFeed variation, U.S. Pat. No. 5,102, 553). Simultaneous advancement is preferred. In certain embodiments, including any of the foregoing embodiments, columns can be operated in parallel groups as described in U.S. Pat. No. 7,618,539 B2. Other useful operating strategies include Modicon (U.S. Pat. No. 7,479,228), SMB internal recirculation (U.S. Pat. No. 8,282,831)

Operating parameters of the SMB apparatus, such as time intervals between advancements of the various introduction and withdrawal sites, the lengths and widths of individual columns, pump pressures, and the mass or volumetric flow rate through each column, will generally be within the ranges used in SMB systems known in the art. Typical columns are packed-bed columns with lengths ranging from 5 to 15 cm and diameters ranging from 2 mm to 1,600 mm. Volumetric relative flow rates calculated per unit column cross section will generally be between 0.5 mL/min/cm$^2$ and 40 mL/min/cm$^2$; pump pressures will generally be between 2 bar and 60 bar, and switch times will generally be from about 0.15 minutes to about 15 minutes.

"Area percent" refers to a percent area under the peak for a compound in an ultra-high performance liquid chromatography (UPLC) or high performance liquid chromatography (HPLC) sample as measured at a designated wavelength. In certain embodiments, including any of the foregoing embodiments, the area percent is measured as a UPLC response at 210 nm compared to the total area of all peaks in the chromatogram. Area percent can be denoted by "A %" or "(A) %" in the methods disclosed herein.

"Weight percent" is based on the total weight of the material obtained and refers to a percent weight of a compound as measured in a UPLC response at a designated wavelength compared to a UPLC response of a standard. In certain embodiments, including any of the foregoing embodiments, the weight percent is measured as a UPLC response at 210 nm compared to a pure tocotrienol standard. In certain embodiments, including any of the foregoing embodiments, the weight percent is measured as a UPLC response at 210 nm compared to a pure alpha-tocotrienol standard. Weight percent can be denoted by "wt %" or "wt. %" or "% (w/w)" in the methods disclosed herein.

The terms "early-eluting impurity compound(s)" and "early-eluting impurities" include any compounds eluting earlier than alpha tocotrienol. In certain embodiments, including any of the foregoing embodiments, the early-eluting impurity compound is a non-alpha-tocotrienol, i.e., the early-eluting impurity is a tocotrienol which is not alpha-tocotrienol.

The terms "late-eluting impurity compound(s)" and "late-eluting impurities" include any compounds eluting later than alpha tocotrienol. In certain embodiments, including any of the foregoing embodiments, the late-eluting impurity compound is one or more tocopherols, or an alpha-tocotrienol-MeOH adduct, where "MeOH" denotes methanol. In certain embodiments, including any of the foregoing embodiments, the late-eluting impurity compound is α-tocopherol.

The term "substantially free of" or "substantially in the absence of" with respect to a composition refers to a composition that includes at least 85% or 90% by weight, in certain embodiments at least 95%, 98%, 99% or 100% by weight, of a designated enantiomer or stereoisomer of a compound. In certain embodiments, including any of the foregoing embodiments, in the methods and compounds provided herein, the compounds are substantially free of other enantiomers or stereoisomers.

Similarly, the term "isolated" with respect to a composition refers to a composition that includes at least 85%, 90%, 95%, 98%, 99% to 100% by weight, of a designated compound, enantiomer, or stereoisomer, the remainder comprising other chemical species, enantiomers, or stereoisomers.

Methods

Enriched alpha-tocotrienol (AT3) compositions can be obtained from tocol mixtures by the methods of the present invention. In particular, high levels of alpha-tocotrienol may be obtained by the methods of the presentation invention. The methods disclosed herein can advantageously be used to obtain high levels of alpha-tocotrienol from tocol mixtures that contain relatively high amounts of non-tocol compounds. For example, the methods disclosed herein can be applied to tocol mixtures having at least 5% phytosterol content. In addition, the methods disclosed herein allow improved recovery of alpha-tocotrienol initially present in the tocol mixtures due to fewer or no separation steps between step (a) and step (b) as described below. Moreover, the methods disclosed herein produce alpha-tocotrienol of high purity using a simulated moving bed (SMB) process.

In one aspect of the invention, a method for making an alpha-tocotrienol enriched tocol mixture is provided, comprising: (a) contacting a tocol mixture with an amino-alkylating agent, wherein the tocol mixture comprises at least one non-alpha tocotrienol, at least one non-tocol, optionally alpha tocotrienol, and optionally one or more tocopherols, whereby the non-alpha tocotrienols are amino-alkylated; (b) reducing the amino-alkylated non-alpha tocotrienols to alpha tocotrienol with a reducing agent; (c) removing one or more waxy impurities from the mixture; (d) contacting the mixture with an agent that binds one or more polar impurities; and (e) removing the agent. In some embodiments, including any of the foregoing embodiments, the tocol mixture is at least about 50%, 55%, 60%, 65%, 70%, 75%, 80%, or 85% tocols. In some embodiments, including any of the foregoing embodiments, there is no intervening step to separate components of the mixture between step (a) and step (b). In some embodiments, including any of the foregoing embodiments, there is no intervening step to separate components of the mixture between step (a) and step (b) other than an optional step to remove water formed from the reaction of step (a).

In some embodiments, the method further includes steps (c)(1) to (c)(4) after step (c), wherein: step (c)(1) comprises converting the alpha tocotrienol to an alpha tocotrienol salt; step (c)(2) comprises providing a polar solvent phase and a non-polar solvent phase and partitioning the alpha tocotrienol salt to the polar solvent phase; step (c)(3) comprises removing the non-polar solvent phase; and step (c)(4) comprises converting the alpha tocotrienol salt in the polar solvent phase to alpha tocotrienol.

In some embodiments, including any of the foregoing embodiments, the method further includes a step (a)(1) after step (a), wherein step (a)(1) comprises removing water formed from the reaction of step (a).

In another aspect of the invention, a method for making an alpha-tocotrienol enriched tocol mixture is provided, comprising: (a) contacting a tocol mixture with an amino-alkylating agent, wherein the tocol mixture comprises at least one non-alpha tocotrienol, at least one non-tocol, optionally alpha tocotrienol, and optionally one or more tocopherols, whereby the non-alpha tocotrienols are amino-alkylated; (b) reducing the amino-alkylated non-alpha tocotrienols to alpha tocotrienol with a reducing agent; (c) removing one or more waxy impurities from the mixture; (c)(1) converting the alpha tocotrienol to an alpha tocotrienol salt; (c)(2) providing a polar solvent phase and a non-polar solvent phase and partitioning the alpha tocotrienol salt to the polar solvent phase; (c)(3) removing the non-polar solvent phase; (c)(4) converting the alpha tocotrienol salt from in polar solvent phase to alpha tocotrienol; (d) contacting the mixture with an agent that binds one or more polar impurities; and (e) removing the agent. In some embodiments, including any of the foregoing embodiments, there is no step to separate components of the mixture between step (a) and step (b). In some embodiments, including any of the foregoing embodiments, the method further includes a step (a)(1) after step (a), wherein step (a)(1) comprises removing water formed from the reaction of step (a). In some embodiments, including any of the foregoing embodiments, the tocol mixture is at least about 50%, 55%, 60%, 65%, or 70% tocols.

In some embodiments, step (a)(1) comprises any method known in the art for removing water from a mixture, which is formed as a by-product of the amino-alkylation reaction. In some embodiments, including any of the foregoing embodiments, step (a)(1) comprises contacting the mixture with a drying agent. Suitable drying agents include, but are not limited to, for example, magnesium sulfate or sodium sulfate. In some embodiments, including any of the foregoing embodiments, step (a)(1) comprises an aqueous wash with brine, followed by contacting the mixture with a drying agent. In some embodiments, including any of the foregoing embodiments, step (a)(1) is carried out in the presence of an organic solvent such as, for example, toluene.

In some embodiments, including any of the foregoing embodiments, step (a)(1) comprises an azeotropic distillation to remove the water. In some embodiments, including any of the foregoing embodiments, step (a)(1) comprises azeotropic distillation in the presence of a solvent with a boiling point of at least 80° C. at 1 atm pressure. In some embodiments, including any of the foregoing embodiments, step (a)(1) comprises azeotropic distillation in the presence of a solvent with a boiling point of at least 95° C. at 1 atm pressure. Suitable solvents include those solvents that can form an azeotrope with water, including, e.g., branched alcohols with a boiling point higher than 80° C. Exemplary solvents include, but are not limited to, 2-butanol, 2-pentanol, 2-methyl-2-butanol, ethanol, toluene, ethyl acetate, acetonitrile, methyl ethyl ketone, cyclohexanol, 2-pentanol, 2-hexanol, or 2-methyl-1-propanol. In some embodiments, the solvent is 2-methyl-2-butanol (also referred to as "t-amyl alcohol" or "t-AmOH").

In some embodiments, including any of the foregoing embodiments, the amino-alkylating agent in step (a) comprises a secondary amine and a formaldehyde equivalent. In some embodiments, including any of the foregoing embodiments, the secondary amine is a cyclic amine (e.g., morpholine, piperidine, pyrrolidine, and N-methyl-piperazine) or a dialkylamines (e.g., dimethylamine, diethylamine, diisopropylamine). In some embodiments, including any of the foregoing embodiments, the secondary amine is N-methyl-piperazine. In some embodiments, including any of the foregoing embodiments, about 2 to about 5 equivalents of the secondary amine with respect to the tocol mixture is used; in some embodiments, including any of the foregoing embodiments, about 2 equivalents, about 2.5 equivalents, about 3 equivalents, about 3.5 equivalents, about 4 equivalents, about 4.5 equivalents, or about 5 equivalents is used. In some embodiments, including any of the foregoing embodiments, the formaldehyde equivalent is paraformaldehyde, a formalin solution (30-40% formaldehyde in water), 1,3,5-trioxane, formaline, formaldehyde gas, or hexamethylenetetramine. In some embodiments, including any of the foregoing embodiments, the formaldehyde equivalent is paraformaldehyde. In some embodiments, including any of the foregoing embodiments, about 1.25 to about 3.5 equivalents of the formaldehyde equivalent with respect to the tocol mixture is used; in some embodiments, including any of the foregoing embodiments, about 1.25 equivalents, about 1.5 equivalents, about 1.75 equivalents, about 2 equivalents, about 2.25 equivalents, about 2.5 equivalents, about 2.75 equivalents, about 3 equivalents, or about 3.5 equivalents is used. The temperature of step (a) can be any temperature deemed suitable by the skilled practitioner. In some embodiments, including any of the foregoing embodiments, the temperature in step (a) before the tocol mixture is contacted with the amino-alkylating agent is about 70° C., or about 75° C., or about 80° C. In some embodiments, including any of the foregoing embodiments, the temperature in step (a) after the tocol mixture is contacted with the amino-alkylating agent is about 100° C., or about 105° C., or about 110° C. In some or any embodiments of step (a) after the amino-alkylated product is formed, the temperature is lowered by the addition of a solvent, such as 2-methyl-2-butanol.

In some embodiments, including any of the foregoing embodiments, the reducing agent in step (b) is a borohydride. The borohydride can be, for example, sodium cyano borohydride (also referred to as "NaCNBH$_3$," or "NaBH$_3$CN"), sodium borohydride, lithium borohydride, or zinc borohydride. In some embodiments, including any of the foregoing embodiments, the reducing agent in step (b) is NaBH$_3$CN. In some embodiments, including any of the foregoing embodiments, about 4 to about 6 equivalents of the reducing agent with respect to the tocol mixture is used; in some embodiments, including any of the foregoing embodiments, about 4 equivalents, about 4.5 equivalents, about 4.75 equivalents, about 5 equivalents, about 5.25 equivalents, about 5.5 equivalents, or about 6 equivalents is used. In some embodiments, including any of the foregoing embodiments, an alcohol having a boiling point of at least about 95° C. is used as a solvent in step (b). In some embodiments, including any of the foregoing embodiments, the solvent in step (b) is a four or five carbon alcohol. In some embodiments, including any of the foregoing embodiments, the solvent in step (b) is 2-hydroxybutanol, 2-hydroxypentanol, or 2-methyl-2-butanol. In some embodiments, including any of the foregoing embodiments, the solvent in step (b) is 2-methyl-2-butanol. In some embodiments, including any of the foregoing embodiments, the temperature in step (b) is about 70° C., or about 75° C., or about 80° C. In some embodiments, including any of the foregoing embodiments, the temperature in step (b) is raised to about 100° C., or about 105° C., or about 107° C., or about 110° C. In some embodiments, including any of the foregoing embodiments, the progression of step (b) can be monitored by HPLC by measuring the amount of starting material remaining. In some embodiments, including any of the foregoing embodiments, step (b) comprises a water quench subsequent to addition of solvent, wherein the water quench and resulting phase split of the reduction step is performed at 60° C. to minimize salt precipitation. In some embodiments, including any of the foregoing embodiments, step (b) comprises a water quench followed by addition of solvent (e.g., heptane or n-heptane), wherein the water quench and resulting phase split of the reduction step is performed at about 20° C.-25° C., after which insoluble solids are filtered.

In some embodiments, including any of the foregoing embodiments, one or more by-products are produced in steps (a) and/or (b), and wherein the mixture optionally comprises residual secondary amine, and wherein the method comprises a step (b)(1) after step (b), wherein step (b)(1) comprises removing at least one of the one or more by-products produced in steps (a) and/or (b) and the optional residual secondary amine. In some embodiments, including any of the foregoing embodiments, step (b)(1) comprises an aqueous work up. In some embodiments, including any of the foregoing embodiments, step (b)(1) comprises contacting the mixture with a solvent and water, filtering the mixture to remove insoluble solid byproducts, and an aqueous work-up of the filtrate. In some embodiments, including any of the foregoing embodiments, the aqueous work up comprises: (i) contacting the mixture with isopropyl acetate, water, and $Na_2HPO_4$, whereby an aqueous phase is formed; (ii) removing the aqueous phase; (iii) performing an acid wash on the non-aqueous phase; and iv) removing the aqueous phase. In some embodiments, the aqueous work up comprises: (i) contacting the mixture with isopropyl acetate and water, whereby an aqueous phase is formed; (ii) removing the aqueous phase; (iii) performing an acid wash on the non-aqueous phase; and iv) removing the aqueous phase. In some embodiments, including any of the foregoing embodiments, the aqueous work up comprises: (i) contacting the mixture with isopropyl acetate and water, whereby an aqueous phase is formed; (ii) removing the aqueous phase; (iii) contacting the mixture with water, whereby an aqueous phase is formed, and removing the aqueous phase; and (iv) performing an acid wash on the non-aqueous phase; and v) removing the aqueous phase. In some embodiments, including any of the foregoing embodiments, the acid wash comprises citric acid. In some embodiments, the acid wash comprises about 5% (w/w), about 7% (w/w), about 10% (w/w), about 12% (w/w), about 15% (w/w), about 18% (w/w), or about 20 (w/w) citric acid. In some embodiments, including any of the foregoing embodiments, the aqueous work up is conducted at about 55° C., at about 60° C., or at about 65° C.

In some embodiments, including any of the foregoing embodiments, step (c) comprises removing solvent that may be present in the mixture and/or cooling to precipitate the one or more waxy impurities. In some embodiments, including any of the foregoing embodiments, some of the solvent which may be present is removed by distillation. In some embodiments, including any of the foregoing embodiments, step (c) comprises performing a solvent exchange to a polar protic solvent. In some embodiments, including any of the foregoing embodiments, the polar protic solvent is methanol. In some embodiments, including any of the foregoing embodiments, step (c) comprises reducing the mixture to about a minimum stir volume. In some embodiments, including any of the foregoing embodiments, step (c) comprises (i) performing a solvent exchange to methanol, (ii) reducing the mixture to about a minimum stir volume, and (iii) cooling the mixture. In some embodiments, including any of the foregoing embodiments, the cooling in step (c) comprises cooling to about −35° C. to about 5° C. In some embodiments, including any of the foregoing embodiments, the cooling in step (c) comprises cooling to about −20° C. to about −10° C. In some embodiments, including any of the foregoing embodiments, the cooling in step (c) comprises cooling to about −35° C. to about −15° C. In some embodiments, including any of the foregoing embodiments, removing the one or more waxy impurities comprises contacting the mixture with a solid binding material. In some embodiments, including any of the foregoing embodiments, removing the one or more waxy impurities comprises contacting the mixture with the solid binding material to produce a slurry, followed by filtering the slurry and retaining the filtrate. In some embodiments, including any of the foregoing embodiments, the solid binding material is a finely divided solid comprising carbon, silica, alumina, or diatomaceous earth. In some embodiments, including any of the foregoing embodiments, the solid binding material is Celite® (diatomaceous earth).

In some embodiments, including any of the foregoing embodiments, step (c) comprises holding the mixture at a temperature of about 15° C. to about 35° C. for a duration of from about 1 to 4 hours and filtering the mixture to remove insoluble byproducts. In some embodiments, the mixture is held at a temperature of from about 15° C. to about 25° C. In some embodiments, the mixture is held at a temperature of from about 20° C. to about 30° C. In some embodiments, the mixture is held at a temperature of from about 22° C. to about 28° C. In some embodiments, the mixture is held at a temperature of about 15° C., 20° C., 25° C., 30° C., or about 35° C. In some embodiments, including any of the foregoing embodiments, the mixture is held at a set temperature or temperature range for from about 1 to about 3 hours, or from about 1 to about 2 hours, or from about 2 to about 4 hours. In some embodiments, including any of the foregoing embodiments, the mixture is held at a set temperature or temperature range for about 1 hour, 2 hours, 3 hours, or 4 hours. In some embodiments, including any of the foregoing embodiments, step (c) comprises an aqueous work up of the mixture. In some embodiments, including any of the foregoing embodiments, the aqueous work up comprises: (i) contacting the mixture with water, whereby an aqueous phase is formed; (ii) removing the aqueous phase; (iii) performing an acid wash on the non-aqueous phase; (iv) removing the aqueous phase. In some embodiments, including any of the foregoing embodiments, the aqueous workup further comprises (v) performing a wash on the non-aqueous phase with water and/or aqueous sodium bicarbonate ($NaHCO_3$) and subsequently removing the aqueous phase. In some embodiments, including any of the foregoing embodiments, the acid wash comprises citric acid. In some embodiments, the acid wash comprises about 5% (w/w), about 7% (w/w), about 10% (w/w), about 12% (w/w), about 15% (w/w), about 18% (w/w), or about 20 (w/w) citric acid.

In some embodiments, including any of the foregoing embodiments, a second solvent is optionally added before the alpha tocotrienol is converted to a salt in step (c)(1). In some embodiments, including any of the foregoing embodiments, the second solvent is a polar solvent such as N-methyl-pyrrolidone (NMP). In some embodiments, including any of the foregoing embodiments, the alpha tocotrienol in step (c)(1) is converted to the alpha tocotrienol salt with an inorganic salt base having a $pK_a$ of more than about 10. In some embodiments, including any of the foregoing embodiments, the inorganic salt base is selected from the group consisting of sodium methoxide (NaOMe), lithium methoxide (LiOMe), potassium methoxide (KOMe), or magnesium methoxide $(Mg(OMe)_2)$. In some embodiments, including any of the foregoing embodiments, the inorganic salt base is NaOMe.

In some embodiments, including any of the foregoing embodiments, the polar solvent phase in step (c)(2) comprises NMP and/or methanol (MeOH). In some embodiments, including any of the foregoing embodiments, the polar solvent phase in step (c)(2) comprises NMP and MeOH. In some embodiments, including any of the foregoing embodiments, the non-polar solvent phase in step (c)(2) comprises an alkane. In some embodiments, including any of the foregoing embodiments, the non-polar solvent phase in step (c)(2) comprises a hexane or a heptane. In some embodiments, including any of the foregoing embodiments, the non-polar solvent phase in step (c)(2) comprises n-heptane. In some embodiments, including any of the foregoing embodiments, the partitioning between the polar and non-polar solvent phases is performed at less than 10° C. In some embodiments, including any of the foregoing embodiments, the partitioning between the polar and non-polar solvent phases is performed at about 0° C.

In some embodiments, including any of the foregoing embodiments, converting the alpha tocotrienol salt to alpha tocotrienol in step (c)(4) comprises addition of an acid having a pH of less than about 7. In some embodiments, including any of the foregoing embodiments, converting the alpha tocotrienol salt to alpha tocotrienol in step (c)(4) comprises addition of HCl; alternatively, in some embodiments, including any of the foregoing embodiments, converting the alpha tocotrienol salt to alpha tocotrienol in step (c)(4) comprises addition of a water-soluble acid with a pKa of 7 or less, for example: acetic acid, formic acid, HBr, $H_3PO_4$, $H_2SO_4$, and carbonic acid. In some embodiments, including any of the foregoing embodiments, step (c)(4) comprises production of a salt by-product, and wherein the method comprises a step (c)(5) after step (c)(4), wherein step (c)(5) comprises removing the salt by-product produced in step (c)(4). In some embodiments, including any of the foregoing embodiments, step (c)(5) comprises solvent extraction with a non-polar light phase, followed by retaining the non-polar light phase. In some embodiments, including any of the foregoing embodiments, the non-polar light phase comprises toluene, any isomers of hexane, heptane, pentane, xylene, or petroleum ether. In some embodiments, including any of the foregoing embodiments, the non-polar light phase is washed with an aqueous wash. In some embodiments, including any of the foregoing embodiments, the non-polar light phase is washed with a brine solution.

In some embodiments, including any of the foregoing embodiments, the agent in step (d) comprises silica, alumina, diatomaceous earth, or clays. In some embodiments, including any of the foregoing embodiments, the solvent(s) in the nonpolar light phase are removed, such as by distillation.

In some embodiments, steps (d) and (e) comprise adding the mixture to a column comprising the agent, and eluting the mixture off the column. In some or any embodiments, solvent is removed to prepare a feed stream at a concentration suitable for SMB purification.

In some embodiments, including any of the foregoing embodiments, the method comprises a step (0 after step (e), wherein step (0 comprises performing a solvent exchange of the mixture with a solvent that is methanol or acetonitrile. In some embodiments, including any of the foregoing embodiments, the solvent exchange is with methanol. In some embodiments, including any of the foregoing embodiments, the solvent exchange is with acetonitrile. In some embodiments, including any of the foregoing embodiments, the solvent exchange is performed in the absence of light and/or protected from exposure to sunlight.

In some embodiments, including any of the foregoing embodiments, the method is performed in the absence of light and/or protected from exposure to sunlight. In some embodiments, including any of the foregoing embodiments, the method partially performed in the absence of light and/or protected from exposure to sunlight. For example, one or more of any of steps (a), (a)(1), (b), (b)(1), (c), (c)(1), (c)(2), (c)(3), (c)(4), (c)(5), (e) and (f) as disclosed herein can be performed in the absence of light and/or protected from exposure to sunlight.

In some or any embodiments, solvent is removed from the product composition to prepare a feed stream at a concentration suitable for SMB purification.

In some embodiments, including any of the foregoing embodiments, the tocol mixture in step (a) is a plant, plant extract, or plant-derived material. In some embodiments, including any of the foregoing embodiments, the tocol mixture is a palm oil or a material derived from palm oil, a palm fruit extract, or a mixture of palm oil and palm fruit extract. In some embodiments, including any of the foregoing embodiments, the tocol mixture is a palm oil. In some embodiments, including any of the foregoing embodiments, the tocol mixture is derived from a palm oil. In some embodiments, the tocol mixture is a commercially available product comprising an enriched tocotrienol extract derived from palm oil. For example, the commercially available product can be one or more products as provided by Carotech, Golden Hope Bioorganic, Davos Life Science, Beijing Gingko Group, Eisai, Eastman Corporation, Oryza Oil & Fat Company, Sime Darby Biorganic Sdn Bhd or Palm Nutraceuticals. In some embodiments, the tocol mixture is Tocomin 50®. In some embodiments, including any of the foregoing embodiments, the phytosterol content of the tocol mixture is at least about 5%, at least about 6%, at least about 7%, at least about 8%, at least about 9%, at least about 10%, at least about 11%, at least about 12%, or at least about 13%, wherein percentage is provided as a weight or area percent. In some embodiments, including any of the foregoing embodiments, the tocol mixture comprises at least about 25 wt. % tocols. In some embodiments, including any of the foregoing embodiments, the tocol mixture comprises at least about 30 wt. % tocols. In some embodiments, including any of the foregoing embodiments, the tocol mixture comprises at least about 35 wt. % tocols. In some embodiments, including any of the foregoing embodiments, the tocol mixture comprises at least about 40 wt. % tocols. In some embodiments, including any of the foregoing embodiments, the tocol mixture comprises at least about 45 wt. % tocols. In some embodiments, including any of the foregoing embodiments, the tocol mixture comprises at least about 50 wt. % tocols. In some embodiments, including any of the foregoing embodiments, the tocol mixture comprises at least about 55 wt. % tocols. In some embodiments, including any of the foregoing embodiments, the tocol mixture comprises at least about 60 wt. % tocols. In some embodiments, including any of the foregoing embodiments, the tocol mixture comprises 65 wt. % tocols. In some embodiments, including any of the foregoing embodiments, the tocol mixture comprises at least about 66 wt. % tocols. In some embodiments, including any of the foregoing embodiments, the tocol mixture comprises at least about 67 wt. % tocols. In some embodiments, including any of the foregoing embodiments, the tocol mixture comprises at least about 68 wt. % tocols. In some embodiments, including any of the foregoing embodiments, the tocol mixture comprises at least about 69 wt. % tocols. In some embodiments, including any of the foregoing embodiments, the tocol mixture comprises at least about 70 wt. % tocols. In some embodiments, the tocol mixture is Gold Tri.E™ 70. In some embodiments, including any of the foregoing embodiments, the tocol mixture comprises at least about 75 wt. % tocols. In some embodiments, including any of the foregoing embodiments, the tocol mixture comprises at least about 76 wt. % tocols. In some embodiments, including any of the foregoing embodiments, the tocol mixture comprises at least about 77 wt. % tocols. In some embodiments, including any of the foregoing embodiments, the tocol mixture comprises at least about 78 wt. % tocols. In some embodiments, including any of the foregoing embodiments, the tocol mixture comprises at least about 79 wt. % tocols. In some embodiments, including any of the foregoing embodiments, the tocol mixture comprises at least about 80 wt. % tocols. In some embodiments, including any of the foregoing embodiments, the tocol mixture comprises at least about 81 wt. % tocols. In some embodiments, including any of the foregoing embodiments, the tocol mixture comprises at least about 82 wt. % tocols. In some embodiments, including any of the foregoing embodiments, the tocol mixture comprises at least about 83 wt. % tocols. In some embodiments, including any of the foregoing embodiments, the tocol mixture comprises at least about 84 wt. % tocols. In some embodiments, including any of the foregoing embodiments, the tocol mixture comprises at least about 85 wt. % tocols. In some embodiments, the tocol mixture is natural palm oil that is a high purity palm tocotrienol product from e.g., Davos Life Science. In some embodiments, the tocol mixture in step (a) contains at least about 65 (A) % tocols, at least about 68 (A) % tocols, or at least about 70 (A) % tocols. In some embodiments, the tocol mixture in step (a) contains about about 84 (A) % of a mixture of tocotrienols and tocopherols.

In some embodiments, including any of the foregoing embodiments, the alpha-tocotrienol in the product composition is the natural form of alpha-tocotrienol, i.e.:

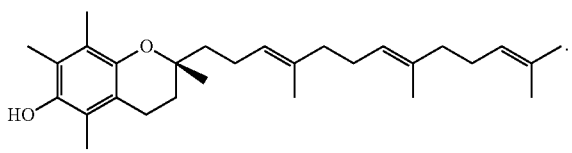 [SMILES: CC(C)=CCC/C(C)=C/CC/C(C)=C/CC[C@]1(C)CCc2c(C)c(O)c(C)c(C)c2O1]

In various embodiments, including any of the foregoing embodiments, the alpha-tocotrienol in the product composition is at least about 80%, at least about 85%, at least about 90%, at least about 91%, at least about 92%, at least about 93%, at least about 94%, at least about 95%, at least about 96%, at least about 97%, at least about 98%, or at least about 99% the natural form of alpha-tocotrienol.

In some embodiments, including any of the foregoing embodiments, the product composition produced by the method for making an alpha-tocotrienol enriched tocol mixture comprises at least about 40 wt. %, at least about 41 wt. %, at least about 42 wt. %, at least about 43 wt. %, at least about 44 wt. %, at least about 45 wt. %, at least about 46 wt. %, at least about 47 wt. %, at least about 48 wt. %, at least about 49 wt. %, at least about 50 wt. %, at least about 51 wt. %, at least about 52 wt. %, at least about 53 wt. %, at least about 54 wt. %, at least about 55 wt. %, at least about 56 wt. %, at least about 57 wt. %, or at least about 58 wt. % alpha-tocotrienol. In some embodiments, including any of the foregoing embodiments, the product composition comprises at least about 59 wt. %, at least about 60 wt. %, at least about 61 wt. %, at least about 62 wt. %, at least about 63 wt. %, at least about 64 wt. %, at least about 65 wt. %, at least about 66 wt. %, at least about 67 wt. %, at least about 68 wt. %, at least about 69 wt. %, or at least about 70 wt. % alpha-tocotrienol.

In some embodiments, including any of the foregoing embodiments, the product composition produced by the method for making an alpha-tocotrienol enriched tocol mixture comprises at least about 50 (A) %, at least about 51 (A) %, at least about 52 (A) %, at least about 53 (A) %, at least about 54 (A) %, at least about 55 (A) %, at least about 56 (A) %, at least about 57 (A) %, or at least about 58 (A) % weight percent alpha-tocotrienol as determined by HPLC or UPLC. In some embodiments, including any of the foregoing embodiments, the product composition comprises at least about 59 (A) %, at least about 60 (A) %, at least about 61 (A) %, at least about 62 (A) %, at least about 63 (A) %, at least about 64 (A) %, at least about 65 (A) %, at least about 66 (A) %, at least about 67 (A) %, at least about 68 (A) %, at least about 69 (A) %, or at least about 70 (A) % alpha-tocotrienol as determined by HPLC or UPLC.

In some embodiments, including any of the foregoing embodiments, the product composition produced by the method for making an alpha-tocotrienol enriched tocol mixture comprises at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, or at least about 85% of the mass of the starting amount of tocol mixture used in step (a).

Also provided herein are methods of purifying a tocotrienol by simulated moving bed chromatography. The methods begin with a feed stream (also referred to as a "feed solution") comprising the tocotrienol and provide a raffinate comprising the tocotrienol in purified form. In certain embodiments, including any of the foregoing embodiments, the methods begin with a feed stream comprising alpha-tocotrienol and provide a raffinate comprising alpha-tocotrienol in purified form. The raffinate is purified relative to the feed stream. In certain embodiments, including any of the foregoing embodiments, the raffinate is substantially purified relative to the feed stream.

In some embodiments, including any of the foregoing embodiments, the methods of purifying a tocotrienol as disclosed herein yield tocotrienol of high purity. In some embodiments, including any of the foregoing embodiments, the tocotrienol purity is in the range of from about 80 wt. % to 99.9 wt. %, or in the range of from about 85 wt. % to 99.9 wt. %, or in the range of from about 90 wt. % to 99.9 wt. %, or in the range of from about 95 wt. % to 99.9 wt. %. In some embodiments, including any of the foregoing embodiments, the tocotrienol purity is in the range of from about 80 wt. % to about 99.9 wt. %, or in the range of from about 85 wt. % to about 99.9 wt. %, or in the range of from about 90 wt. % to about 99.9 wt. %, or in the range of from about 95 wt. % to about 99.9 wt. %. In some embodiments, including any of the foregoing embodiments, the tocotrienol purity is greater than 80 wt. %, or greater than 85 wt. %, or greater than 90 wt. %, or greater than 91 wt. %, or greater than 92 wt. %, or greater than 93 wt. %, or greater than 94 wt. %, or greater than 95 wt. %, or greater than 96 wt. %, or greater than 97 wt. %, or greater than 98 wt. %, or greater than 99 wt. %, or greater than 99.5 wt. %, or greater than 99.9 wt. %. In some embodiments, including any of the foregoing embodiments, the tocotrienol purity is more than about 80 wt. %, or more than about 85 wt. %, or more than about 90 wt. %, or more than about 91 wt. %, or more than about 92 wt. %, or more than about 93 wt. %, or more than about 94 wt. %, or more than about 95 wt. %, or more than about 96 wt. %, or more than about 97 wt. %, or more than about 98 wt. %, or more than about 99 wt. %, or more than about 99.5 wt. %, or more than about 99.9 wt. %. In some embodiments, including any of the foregoing embodiments, the impurities in the final product are less than about 20 wt. %, or less than about 15 wt. %, or less than about 10 wt. %, or less than about 5 wt. %, or less than about 4 wt. %, or less than about 3 wt. %, or less than about 2 wt. %, or less than about 1 wt. %, or less than about 0.5 wt. %, or less than about 0.1 wt. %. In some embodiments, including any of the foregoing embodiments, the impurities in the final product comprise tocols or tocol derivatives in the final product and total less than about 5 wt. %, less than about 4 wt. %, less than about 3 wt. %, less than about 2 wt. %, less than about 1 wt. %, less than about 0.5 wt. % or less than about 0.1 wt. %. In some embodiments, including any of the foregoing embodiments, the impurities in the final product consist of tocols or tocol derivatives in the final product and total less than about 5 wt. %, less than about 4 wt. %, less than about 3 wt. %, less than about 2 wt. %, less than about 1 wt. %, less than about 0.5 wt. % or less than about 0.1 wt. %. In some embodiments, solvents which can be readily removed by evaporation are not considered as impurities when determining the percentage purity of a composition or the percentage of impurities present in a composition.

In some embodiments, including any of the foregoing embodiments, the tocotrienol purity is in the range of from about 80 (A) % to 99.9 (A) %, or in the range of from about 85 (A) % to 99.9 (A) %, or in the range of from about 90 (A) % to 99.9 (A) %, or in the range of from about 95 (A) % to 99.9 (A) %. In some embodiments, including any of the foregoing embodiments, the tocotrienol purity is in the range of from about 80 (A) % to about 99.9 (A) %, or in the range of from about 85 (A) % to about 99.9 (A) %, or in the range of from about 90 (A) % to about 99.9 (A) %, or in the range of from about 95 (A) % to about 99.9 (A) %. In some embodiments, including any of the foregoing embodiments, the tocotrienol purity is greater than 80 (A) %, or greater than 85 (A) %, or greater than 90 (A) %, or greater than 91 (A) %, or greater than 92 (A) %, or greater than 93 (A) %, or greater than 94 (A) %, or greater than 95 (A) %, or greater than 96 (A) %, or greater than 97 (A) %, or greater than 98 (A) %, or greater than 99 (A) %, or greater than 99.5 (A) %, or greater than 99.9 (A) %. In some embodiments, including any of the foregoing embodiments, the tocotrienol purity is more than about 80 (A) %, or more than about 85 (A) %, or more than about 90 (A) %, or more than about 91 (A) %, or more than about 92 (A) %, or more than about 93 (A) %, or more than about 94 (A) %, or more than about 95 (A) %, or more than about 96 (A) %, or more than about 97 (A) %, or more than about 98 (A) %, or more than about 99 (A) %, or more than about 99.5 (A) %, or more than about 99.9 (A) %. In some embodiments, including any of the foregoing embodiments, the impurities in the final product are less than about 20 (A) %, or less than about 15 (A) %, or less than about 10 (A) %, or less than about 5 (A) %, or less than about 4 (A) %, or less than about 3 (A) %, or less than about 2 (A) %, or less than about 1 (A) %, or less than about 0.5 (A) %, or less than about 0.1 (A) %. In some embodiments, including any of the foregoing embodiments, the impurities in the final product comprise tocols or tocol derivatives in the final product and total less than about 5 (A) %, less than about 4 (A) %, less than about 3 (A) %, less than about 2 (A) %, less than about 1 (A) %, less than about 0.5 (A) % or less than about 0.1 (A) %. In some embodiments, including any of the foregoing embodiments, the impurities in the final product consist of tocols or tocol derivatives in the final product and total less than about 5 (A) %, less than about 4 (A) %, less than about 3 (A) %, less than about 2 (A) %, less than about 1 (A) %, less than about 0.5 (A) % or less than about 0.1 (A) %. In some embodiments, solvents which can be readily removed by evaporation are not considered as impurities when determining the percentage purity of a composition or the percentage of impurities present in a composition.

In some embodiments, including any of the foregoing embodiments, the methods of purifying a tocotrienol as disclosed herein yield alpha-tocotrienol of high purity. In some embodiments, including any of the foregoing embodiments, the alpha-tocotrienol purity is in the range of from about 80 wt. % to 99.9 wt. %, or in the range of from about 85 wt. % to 99.9 wt. %, or in the range of from about 90 wt. % to 99.9 wt. %, or in the range of from about 95 wt. % to 99.9 wt. %. In some embodiments, including any of the foregoing embodiments, the alpha-tocotrienol purity is in the range of from about 80 wt. % to about 99.9 wt. %, or in the range of from about 85 wt. % to about 99.9 wt. %, or in the range of from about 90 wt. % to about 99.9 wt. %, or in the range of from about 95 wt. % to about 99.9 wt. %. In some embodiments, including any of the foregoing embodiments, the alpha-tocotrienol purity is greater than 80 wt. %, or greater than 85 wt. %, or greater than 90 wt. %, or greater than 91 wt. %, or greater than 92 wt. %, or greater than 93 wt. %, or greater than 94 wt. %, or greater than 95 wt. %, or greater than 96 wt. %, or greater than 97 wt. %, or greater than 98 wt. %, or greater than 99 wt. %, or greater than 99.5 wt. %, or greater than 99.9 wt. %. In some embodiments, including any of the foregoing embodiments, the alpha-tocotrienol purity is more than about 80 wt. %, or more than about 85 wt. %, or more than about 90 wt. %, or more than about 91 wt. %, or more than about 92 wt. %, or more than about 93 wt. %, or more than about 94 wt. %, or more than about 95 wt. %, or more than about 96 wt. %, or more than about 97 wt. %, or more than about 98 wt. %, or more than about 99 wt. %, or more than about 99.5 wt. %, or more than about 99.9 wt. %. In some embodiments, including any of the foregoing embodiments, the impurities in the final product are less than about 20 wt. %, or less than about 15 wt. %, or less than about 10 wt. %, or less than about 5 wt. %, or less than about 4 wt. %, or less than about 3 wt. %, or less than about 2 wt. %, or less than about 1 wt. %, or less than about 0.5 wt. %, or less than about 0.1 wt. %. In some embodiments, including any of the foregoing embodiments, the impurities comprise tocols or tocol derivatives in the final product and total less than about 5 wt. %, less than about 4 wt. %, less than about 3 wt. %, less than about 2 wt. %, less than about 1 wt. %, less than about 0.5 wt. % or less than about 0.1 wt. %. In some embodiments, including any of the foregoing embodiments, the impurities consist of tocols or tocol derivatives in the final product and total less than about 5 wt. %, less than about 4 wt. %, less than about 3 wt. %, less than about 2 wt. %, less than about 1 wt. %, less than about 0.5 wt. % or less than about 0.1 wt. %. In some embodiments, solvents which can be readily removed by evaporation are not considered as impurities when determining the percentage purity of a composition or the percentage of impurities present in a composition.

In some embodiments, including any of the foregoing embodiments, the alpha-tocotrienol purity is in the range of from about 80 (A) % to 99.9 (A) %, or in the range of from about 85 (A) % to 99.9 (A) %, or in the range of from about 90 (A) % to 99.9 (A) %, or in the range of from about 95 (A) % to 99.9 (A) %. In some embodiments, including any of the foregoing embodiments, the alpha-tocotrienol purity is in the range of from about 80 (A) % to about 99.9 (A) %, or in the range of from about 85 (A) % to about 99.9 (A) %, or in the range of from about 90 (A) % to about 99.9 (A) %, or in the range of from about 95 (A) % to about 99.9 (A) %. In some embodiments, including any of the foregoing embodiments, the alpha-tocotrienol purity is greater than 80 (A) %, or greater than 85 (A) %, or greater than 90 (A) %, or greater than 91 (A) %, or greater than 92 (A) %, or greater than 93 (A) %, or greater than 94 (A) %, or greater than 95 (A) %, or greater than 96 (A) %, or greater than 97 (A) %, or greater than 98 (A) %, or greater than 99 (A) %, or greater than 99.5 (A) %, or greater than 99.9 (A) %. In some embodiments, including any of the foregoing embodiments, the alpha-tocotrienol purity is more than about 80 (A) %, or more than about 85 (A) %, or more than about 90 (A) %, or more than about 91 (A) %, or more than about 92 (A) %, or more than about 93 (A) %, or more than about 94 (A) %, or more than about 95 (A) %, or more than about 96 (A) %, or more than about 97 (A) %, or more than about 98 (A) %, or more than about 99 (A) %, or more than about 99.5 (A) %, or more than about 99.9 (A) %. In some embodiments, including any of the foregoing embodiments, the impurities in the final product are less than about 20 (A) %, or less than about 15 (A) %, or less than about 10 (A) %, or less than about 5 (A) %, or less than about 4 (A) %, or less than about 3 (A) %, or less than about 2 (A) %, or less than about 1 (A) %, or less than about 0.5 (A) %, or less than about 0.1 (A) %. In some embodiments, including any of the foregoing embodiments, the impurities in the final product comprise tocols or tocol derivatives in the final product and total less than about 5 (A) %, less than about 4 (A) %, less than about 3 (A) %, less than about 2 (A) %, less than about 1 (A) %, less than about 0.5 (A) % or less than about 0.1 (A) %. In some embodiments, including any of the foregoing embodiments, the impurities in the final product consist of tocols or tocol derivatives in the final product and total less than about 5 (A) %, less than about 4 (A) %, less than about 3 (A) %, less than about 2 (A) %, less than about 1 (A) %, less than about 0.5 (A) % or less than about 0.1 (A) %. In some embodiments, solvents which can be readily removed by evaporation are not considered as impurities when determining the percentage purity of a composition or the percentage of impurities present in a composition.

The feed stream can be any composition comprising the tocotrienol. In certain embodiments, including any of the foregoing embodiments, the feed stream can be any composition comprising alpha-tocotrienol. In advantageous embodiments, the feed stream is derived from, or the same as, a product composition of any of the methods described in the sections above. In certain embodiments, including any of the foregoing embodiments, the product composition is adjusted for use as a feed stream. The feed stream generally comprises one or more impurity compounds in addition to the tocotrienol. In certain embodiments, including any of the foregoing embodiments, the feed stream generally comprises one or more impurity compounds in addition to alpha-tocotrienol. Impurity compounds are described below. Advantageously, the methods are capable of purifying the tocotrienol from the impurity compound or compounds. In certain embodiments, including any of the foregoing embodiments, advantageously, the methods are capable of purifying alpha-tocotrienol from the impurity compound or compounds.

The tocotrienol can be any tocotrienol known to those of skill in the art. In certain embodiments, including any of the foregoing embodiments, the tocotrienol can be selected from the group consisting of alpha tocotrienol, beta tocotrienol, gamma tocotrienol, and delta tocotrienol. In particular embodiments, the tocotrienol is alpha tocotrienol.

The impurity compounds can be any compound other than the tocotrienol in the feed stream. In some embodiments, including any of the foregoing embodiments, the impurity compounds can be any compound other than alpha-tocotrienol in the feed stream. Typically, the impurity compounds are compounds that the practitioner of skill desires to eliminate from the composition. In certain embodiments, including any of the foregoing embodiments, the impurity compounds are selected from tocotrienols other than a desired tocotrienol (e.g., alpha-tocotrienol). For instance, in methods of purifying alpha tocotrienol, the one or more impurity compounds can be any or all of beta tocotrienol, gamma tocotrienol, delta tocotrienol, and tocopherols (alpha-, beta-, gamma-, or delta-tocopherol). In addition, the impurity compounds can also be selected from derivatives of the desired tocotrienol (in some embodiments, alpha-tocotrienol) and other impurities, including non-tocol impurities, from prior reaction or processing steps or that may be present in the starting material.

In some embodiment, including any of the foregoing embodiments, the analytical method used to determine purity is according to:

| Run Parameter | Conditions | | |
|---|---|---|---|
| Column | HALO RP-Amide, 2.7 μm, 150 * 3 mm | | |
| Column Temperature | 40° C. | | |
| Temperature of autosampler | 4° C. | | |
| Flow | 1.4 mL/min | | |
| Mobile Phases | Mobile Phase A = 100% water Mobile Phase B = 80% acetonitrile:20% methanol | | |
| | Time (min) | % A | % B |
| Gradient | 0 | 60 | 40 |
| | 44.0 | 0 | 100 |
| | 52.0 | 0 | 100 |

| Run Parameter | Conditions | | |
|---|---|---|---|
| | 54.0 | 60 | 40 |
| | 61.0 | 60 | 40 |
| Sample diluent | Tetrahydrofuran | | |
| Injection Volume | 5.0 µL | | |
| Sample Concentration (Nominal Target) | 0.5 mg/mL | | |
| Detection | UV: 210 nm (bandwidth 4 nm when using a DAD) | | |
| Retention time | alpha-tocotrienol: ca. 26.8 min (RRT: 1.00) | | |

In some embodiments, including any of the foregoing embodiments, an alpha tocotrienol-MeOH adduct is one of the impurities in the feed stream used in the first and/or second pass SMB purification(s). In some embodiments, including any of the foregoing embodiments, the alpha tocotrienol-MeOH adduct has a relative retention time (RRT) of about 0.985 in an UPLC analysis, as measured at a wavelength of 210 nm. In some embodiments, including any of the foregoing embodiments, the alpha tocotrienol-MeOH adduct has the following structure:

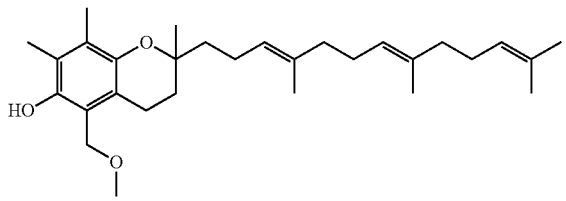 [SMILES: COCc1c(O)c(C)c(C)c2c1CCC(C)(CC/C=C(\C)CC/C=C(\C)CCC=C(C)C)O2]

In certain embodiments, including any of the foregoing embodiments, the feed stream contains greater than or equal to about 45 wt %, greater than or equal to about 50 wt %, greater than or equal to about 55 wt %, greater than or equal to about 60 wt %, greater than or equal to about 65 wt %, greater than or equal to about 70 wt %, greater than or equal to about 75 wt %, or greater than or equal to about 80 wt %, of the alpha-, beta-, gamma-, or delta-tocotrienol, including as compared to the non-target tocotrienols. In certain embodiments, including any of the foregoing embodiments, the feed stream contains about 50 wt %, about 51 wt %, about 52 wt %, about 53 wt %, about 54 wt %, about 55 wt %, about 56 wt %, about 57 wt %, about 58 wt %, about 59 wt %, about 60 wt %, about 61 wt %, about 62 wt %, about 63 wt %, about 64 wt %, about 65 wt %, about 66 wt %, about 67 wt %, about 68 wt %, about 69 wt %, about 70 wt %, about 71 wt %, about 72 wt %, about 73 wt %, about 74 wt %, about 75 wt %, about 76 wt %, about 77 wt %, about 78 wt %, about 79 wt %, about 80 wt %, about 81 wt %, about 82 wt %, about 83 wt %, about 84 wt %, or about 85 wt %, of the alpha-, beta-, gamma-, or delta-tocotrienol, including as compared to the non-target tocotrienols. In certain embodiments, including any of the foregoing embodiments, the feed stream contains greater than or equal to about 45 wt %, greater than or equal to about 50 wt %, greater than or equal to about 55 wt %, greater than or equal to about 60 wt %, greater than or equal to about 65 wt %, greater than or equal to about 70 wt %, greater than or equal to about 75 wt %, or greater than or equal to about 80 wt %, of the alpha-tocotrienol. In certain embodiments, including any of the foregoing embodiments, the feed stream contains about 50 wt %, about 51 wt %, about 52 wt %, about 53 wt %, about 54 wt %, about 55 wt %, about 56 wt %, about 57 wt %, about 58 wt %, about 59 wt %, about 60 wt %, about 61 wt %, about 62 wt %, about 63 wt %, about 64 wt %, about 65 wt %, about 66 wt %, about 67 wt %, about 68 wt %, about 69 wt %, about 70 wt %, about 71 wt %, about 72 wt %, about 73 wt %, about 74 wt %, about 75 wt %, about 76 wt %, about 77 wt %, about 78 wt %, about 79 wt %, about 80 wt %, about 81 wt %, about 82 wt %, about 83 wt %, about 84 wt %, or about 85 wt %, of the alpha-tocotrienol.

In certain embodiments, including any of the foregoing embodiments, the feed stream contains greater than or equal to about 60 (A) %, greater than or equal to about 65 (A) %, greater than or equal to about 70 (A) %, greater than or equal to about 75 (A) %, greater than or equal to about 80 (A) %, or greater than or equal to about 85 (A) %, of the alpha-, beta-, gamma-, or delta-tocotrienol, including as compared to the non-target tocotrienols. In certain embodiments, including any of the foregoing embodiments, the feed stream contains about 60 (A) %, about 61 (A) %, about 62 (A) %, about 63 (A) %, about 64 (A) %, about 65 (A) %, about 66 (A) %, about 67 (A) %, about 68 (A) %, about 69 (A) %, about 70 (A) %, about 71 (A) %, about 72 (A) %, about 73 (A) %, about 74 (A) %, about 75 (A) %, about 76 (A) %, about 77 (A) %, about 78 (A) %, about 79 (A) %, about 80 (A) %, about 81 (A) %, about 82 (A) %, about 83 (A) %, about 84 (A) %, or about 85 (A) %, of the alpha-, beta-, gamma-, or delta-tocotrienol, including as compared to the non-target tocotrienols. In certain embodiments, including any of the foregoing embodiments, the feed stream contains greater than or equal to about 60 (A) %, greater than or equal to about 65 (A) %, greater than or equal to about 70 (A) %, greater than or equal to about 75 (A) %, greater than or equal to about 80 (A) %, or greater than or equal to about 85 (A) %, of the alpha-tocotrienol. In certain embodiments, including any of the foregoing embodiments, the feed stream contains about 60 (A) %, about 61 (A) %, about 62 (A) %, about 63 (A) %, about 64 (A) %, about 65 (A) %, about 66 (A) %, about 67 (A) %, about 68 (A) %, about 69 (A) %, about 70 (A) %, about 71 (A) %, about 72 (A) %, about 73 (A) %, about 74 (A) %, about 75 (A) %, about 76 (A) %, about 77 (A) %, about 78 (A) %, about 79 (A) %, about 80 (A) %, about 81 (A) %, about 82 (A) %, about 83 (A) %, about 84 (A) %, or about 85 (A) %, of the alpha-tocotrienol.

In some embodiments, the feed stream for SMB purification is prepared using material made using procedures described in Example 1. In certain embodiments, the material prepared in Example 1 is used directly as the feed stream. In certain embodiments, the material prepared in Example 1 is diluted to a concentration suitable for a feed stream to be used in SMB purification. The feed stream comprises one or more solvents. In certain embodiments, the feed stream comprises methanol. In certain embodiments, the feed stream comprises the compounds dissolved in methanol. In some embodiments, the feed stream consists essentially of the compounds dissolved in methanol. The compounds can include the desired tocotrienol (in some embodiments, alpha-tocotrienol) and any impurity compounds. In certain embodiments, an oil comprising the desired tocotrienol (in some embodiments, alpha-tocotrienol) is diluted in methanol for the feed stream.

In some embodiments, the feed stream for SMB purification is prepared using material made using procedures described in Example 3. In certain embodiments, the material prepared in Example 3 is used directly as the feed stream. In certain embodiments, the material prepared in Example 3 is diluted to a concentration suitable for a feed stream to be used in SMB purification. The feed stream can comprise one or more solvents. In certain embodiments, the feed stream comprises acetonitrile, a heptane (in some embodiments, n-heptane), and/or water. In certain embodiments, the feed stream comprises acetonitrile and a heptane (in some embodiments, n-heptane), or water. In certain embodiments, the feed stream comprises acetonitrile. In certain embodiments, the feed stream comprises the compounds dissolved in acetonitrile, a heptane (in some embodiments, n-heptane), and/or water; and optionally any residual toluene from the previous step. In certain embodiments, the feed stream consists essentially of the compounds dissolved in acetonitrile and a heptane (in some embodiments, n-heptane), or water; and optionally any residual toluene from the previous step. In certain embodiments, the feed stream comprises the compounds dissolved in acetonitrile. In certain embodiments, the feed stream consists essentially of the compounds dissolved in acetonitrile. In certain embodiments, the feed stream comprises the compounds dissolved in acetonitrile and optionally any residual toluene from the previous step. In certain embodiments, the feed stream consists essentially of the compounds dissolved in acetonitrile and optionally any residual toluene from the previous step. The compounds can include the desired tocotrienol (in some embodiments, alpha-tocotrienol) and any impurity compounds. In certain embodiments, an oil comprising the desired tocotrienol (in some embodiments, alpha-tocotrienol) is diluted in acetonitrile for the feed stream.

In some embodiments, the feed stream for SMB purification is prepared using material made using procedures described in Example 6. In certain embodiments, the material prepared in Example 6 is used directly as the feed stream. In certain embodiments, the material prepared in Example 6 is diluted to a concentration suitable for a feed stream to be used in SMB purification. The feed stream can comprise one or more solvents. In some embodiments, the feed stream comprises acetonitrile, a heptane (in some embodiments, n-heptane), t-AmOH, and/or water. In some embodiments, the feed stream comprises acetonitrile, a heptane (in some embodiments, n-heptane), and t-AmOH. In some embodiments, the feed stream comprises acetonitrile and a heptane (in some embodiments, n-heptane). In some embodiments, the feed stream comprises acetonitrile and t-AmOH. In some embodiments, the feed stream comprises acetonitrile and water. In some embodiments, the feed stream comprises acetonitrile. In certain embodiments, the feed stream comprises the compounds dissolved in acetonitrile, a heptane (in some embodiments, n-heptane), t-AmOH, and/or water. In some embodiments, the feed stream comprises the compounds dissolved in acetonitrile, a heptane (in some embodiments, n-heptane), and t-AmOH. In some embodiments, the feed stream comprises the compounds dissolved in acetonitrile and a heptane (in some embodiments, n-heptane). In some embodiments, the feed stream comprises the compounds dissolved in acetonitrile and t-AmOH. In some embodiments, the feed stream comprises the compounds dissolved in acetonitrile and water. In some embodiments, the feed stream comprises the compounds dissolved in acetonitrile. In some embodiments, the feed stream consists essentially of the compounds dissolved in acetonitrile, a heptane (in some embodiments, n-heptane), t-AmOH, and/or water. In some embodiments, the feed stream consists essentially of the compounds dissolved in acetonitrile, a heptane (in some embodiments, n-heptane), and t-AmOH. In some embodiments, the feed stream consists essentially of the compounds dissolved in acetonitrile and a heptane (in some embodiments, n-heptane). In some embodiments, the feed stream consists essentially of the compounds dissolved in acetonitrile and t-AmOH. In some embodiments, the feed stream consists essentially of the compounds dissolved in acetonitrile and water. In some embodiments, the feed stream consists essentially of the compounds dissolved in acetonitrile. The compounds can include the desired tocotrienol (in some embodiments, alpha-tocotrienol) and any impurity compounds. In certain embodiments, an oil comprising the desired tocotrienol (in some embodiments, alpha-tocotrienol) is diluted in acetonitrile is provided for the feed stream.

The feed stream can be applied to the SMB apparatus, or the feed stream can be pre-treated. In certain embodiments, including any of the foregoing embodiments, the feed stream is treated by passing through one or more silica plugs to remove some impurities. In certain embodiments, including any of the foregoing embodiments, the solvent in the effluent from the silica plug treatment is removed to achieve a concentration suitable for SMB purification.

The feed stream can comprise the compounds in any concentration deemed suitable to the practitioner of skill. In particular embodiments, the concentration is from about 1 to about 200 g/L, from about 5 to about 200 g/L, from about 10 to about 200 g/L, from about 20 to about 200 g/L, or from about 25 to about 200 g/L. In particular embodiments, the concentration is about 38 g/L. In particular embodiments, the concentration is about 130 g/L. In particular embodiments, the concentration is about 150 g/L.

In some embodiments, the eluant comprises methanol. In some embodiments, the eluant comprises acetonitrile. In some embodiments, the eluant comprises acetonitrile and a heptane (in some embodiments, n-heptane). In some embodiments, the eluant comprises acetonitrile and water. In some embodiments, the eluant comprises acetonitrile, a heptane (e.g., n-heptane), and t-AmOH. In some embodiments, the eluant comprises acetonitrile and t-AmOH. In some embodiments, the eluant comprises acetonitrile, a heptane (e.g., n-heptane), t-AmOH, and/or water.

The stationary phase of the SMB apparatus can be any stationary phase deemed suitable by the practitioner of skill. In certain embodiments, including any of the foregoing embodiments, the stationary phase comprises a silica gel. In certain embodiments, including any of the foregoing embodiments, the stationary phase comprises a $C_{18}$ silica gel. In certain embodiments, including any of the foregoing embodiments, the stationary phase comprises a non silica based packing material (including a polymeric resin).

In particular embodiments, the stationary phase comprises a Chromatorex end-capped C18 hydrophobic silica gel (Fuji). In particular embodiments, the stationary phase comprises a Chromatorex $C_{18}$ hydrophobic silica gel, and the feed stream comprises methanol. In particular embodiments, the stationary phase comprises a Chromatorex $C_{18}$ hydrophobic silica gel, and the feed stream comprises acetonitrile.

In some embodiments, the stationary phase comprises an Ace 10 C18-AR silica bonded packing material (Advanced Chromatography Technologies Ltd.). In particular embodiments, the stationary phase comprises an Ace 10 C18-AR silica bonded packing material, and the feed stream comprises acetonitrile. In some embodiments, the eluant comprises acetonitrile and water.

In some embodiments, the stationary phase comprises a reversed phase gel. In certain embodiments, the stationary phase comprises a polystyrene gel. In certain embodiments, the stationary phase comprises an MCI CHP20 gel (Mitsubishi). In particular embodiments, the stationary phase comprises an MCI CHP20/P20 gel (Mitsubishi). In particular embodiments, the stationary phase comprises an MCI CHP20/P20 gel, and the feed stream comprises acetonitrile. In some embodiments, the eluant comprises acetonitrile and a heptane (in some embodiments, n-heptane).

In some embodiments, the stationary phase comprises Mac Mod C18 AR 15-20 micron packing material. In some embodiments, the stationary phase comprises Mac Mod C18 AR 15-20 micron packing material, and the feed stream comprises acetonitrile.

The stationary phase can have any size deemed suitable by the practitioner of skill. In certain embodiments, including any of the foregoing embodiments, the stationary phase has a particle size from about 10 microns to about 100 microns. In certain embodiments, including any of the foregoing embodiments, the stationary phase has a particle size from about 10 microns to about 25 microns. In certain embodiments, including any of the foregoing embodiments, the stationary phase has a particle size of about 10 microns, about 15 microns, about 20 microns, about 25 microns, about 30 microns, about 35 microns, about 40 microns, about 50 microns, about 60 microns, about 70 microns, about 80 microns, about 90 microns, or about 100 microns.

The columns of the SMB apparatus can have any size deemed suitable by the practitioner of skill. In certain embodiments, including any of the foregoing embodiments, the columns have a diameter of about 4.6 mm to about 1000 mm. In certain embodiments, including any of the foregoing embodiments, the columns have a diameter of about 1 cm to about 10 cm. In certain embodiments, including any of the foregoing embodiments, the columns have a length of about 5 cm to about 1 meter. In certain embodiments, including any of the foregoing embodiments, the columns have a length of about 10 cm to about 1 meter. The practitioner of skill can increase the column size with the scale of the purification method.

The SMB apparatus can have any number of columns deemed suitable by the practitioner of skill. In certain embodiments, including any of the foregoing embodiments, the SMB apparatus has at least 3, 4, 5, 6, 7, or 8 columns. The practitioner of skill can increase the number of columns with the scale of the purification method.

The SMB apparatus can be run at any throughput deemed suitable by the practitioner of skill. In certain embodiments, including any of the foregoing embodiments, the throughput is from about 0.05 kg oil per kg stationary phase per 24 hours to about 3 kg oil per kg stationary phase per 24 hours. In certain embodiments, including any of the foregoing embodiments, the throughput is at least 0.05 kg oil per kg stationary phase per 24 hours. In certain embodiments, including any of the foregoing embodiments, the throughput is at least 0.10 kg oil per kg stationary phase per 24 hours. In certain embodiments, including any of the foregoing embodiments, the throughput is at least 0.20 kg oil per kg stationary phase per 24 hours. In certain embodiments, including any of the foregoing embodiments, the throughput is at least 0.25 kg oil per kg stationary phase per 24 hours. In certain embodiments, including any of the foregoing embodiments, the throughput is at least 0.30 kg oil per kg stationary phase per 24 hours. In certain embodiments, including any of the foregoing embodiments, the throughput is at least 0.40 kg oil per kg stationary phase per 24 hours. In certain embodiments, including any of the foregoing embodiments, the throughput is at least 0.50 kg oil per kg stationary phase per 24 hours. In certain embodiments, including any of the foregoing embodiments, the throughput is at least 0.60 kg oil per kg stationary phase per 24 hours. In certain embodiments, including any of the foregoing embodiments, the throughput is at least 0.75 kg oil per kg stationary phase per 24 hours. In certain embodiments, including any of the foregoing embodiments, the throughput is at least 0.90 kg oil per kg stationary phase per 24 hours. In certain embodiments, including any of the foregoing embodiments, the throughput is at least 0.95 kg oil per kg stationary phase per 24 hours. In certain embodiments, including any of the foregoing embodiments, the throughput is at least 1 kg oil per kg stationary phase per 24 hours. The mass of the oil refers to the oil comprising tocotrienol that is used to prepare the feed stream.

The SMB apparatus can be run at any pressure deemed suitable to the practitioner of skill. In certain embodiments, including any of the foregoing embodiments, the SMB apparatus is run at a pressure from about 2 bar to about 100 bar. In certain embodiments, including any of the foregoing embodiments, the SMB apparatus is run at a pressure from about 15 bar to about 45 bar. In particular embodiments, the SMB apparatus is at a pressure of about 15 bar, about 20 bar, about 25 bar, about 30 bar, about 35 bar, about 40 bar, or about 45 bar.

The SMB flow rates can be any flow rates deemed suitable by the practitioner of skill. In particular embodiments, the flow rates are from about 1 mL/min to about 20 mL min. In certain embodiments, including any of the foregoing embodiments, the flow rates are from about 1 mL/min to about 15 mL/min. The flow rates can be the same, or each flow rate can preferably be adjusted independently by the practitioner of skill. The flow rates include the eluent flow rate, the feed flow rate, the extract flow rate, the raffinate flow rate, and the recycle flow rate. A skilled practitioner would know how to scale the flow rates as a function of the columns diameter.

The SMB switch time can be any switch time deemed suitable by the practitioner of skill. In certain embodiments, including any of the foregoing embodiments, the switch time is from about 1 to about 15 minutes. In certain embodiments, including any of the foregoing embodiments, the switch time is from about 1 to about 10 minutes. In particular embodiments, the switch time is about 1 minute, about 2 minutes, about 3 minutes, about 4 minutes, about 5 minutes, about 6 minutes, about 7 minutes, about 8 minutes, about 9 minutes, or about 10 minutes.

The SMB method can be conducted at any temperature deemed suitable to the practitioner of skill. In certain embodiments, including any of the foregoing embodiments, the temperature is from about 20° C. to about 55° C. In some embodiments, the temperature is about 20° C., about 25° C., about 30° C., about 35° C., about 40° C., about 45° C., about 50° C., or about 55° C. In some embodiments, the temperature is about 25° C. In some embodiments, the temperature is about 28° C. In some embodiments, the temperature is about 30° C. In some embodiments, the temperature is about 32° C. In some embodiments, the temperature is about 35° C.

In some embodiments, the feed stream temperature is from about 20° C. to about 55° C. In some embodiments, the temperature is about 20° C., about 25° C., about 30° C., about 35° C., about 40° C., about 45° C., about 50° C., or about 55° C. In some embodiments, the feed stream temperature is about 40° C. In some embodiments, the feed stream temperature is about 45° C. In some embodiments, the feed stream temperature is about 50° C.

In certain embodiments, including any of the foregoing embodiments, the SMB method is run one time. Advantageously, further purification can be achieved by running the SMB method more than once. Accordingly, in certain embodiments, including any of the foregoing embodiments, the SMB method is run with one pass, with two passes, with three passes, or with more than three passes. In some embodiments, the SMB method is run with one pass. In some embodiments, the SMB method is run with two passes. In some embodiments, the SMB method is run with three passes.

The SMB method can proceed for any time deemed suitable for purification of the tocotrienol. In particular embodiments, the method proceeds for about 6 hours, about 12 hours, about 18 hours, about 24 hours, about 36 hours, about 48 hours, about 60 hours, about 72 hours, about 84 hours, or about 96 hours. In some embodiments, the method proceeds for about 24 hours. In some embodiments, the method proceeds for from about 24 to 36 hours. In some embodiments, the method proceeds for about 36 hours. In some embodiments, the method proceeds for from about 36 to 48 hours. In some embodiments, the method proceeds for about 48 hours. In some embodiments, the method proceeds for from about 48 to 60 hours. In some embodiments, the method proceeds for about 60 hours. Purification progress can be monitored by standard techniques such as thin layer chromatography or high-performance liquid chromatography. In certain embodiments, including any of the foregoing embodiments, the first pass purification removes the late-eluting impurities. In certain embodiments, including any of the foregoing embodiments, the second pass removes the early-eluting impurities. In certain embodiments, including any of the foregoing embodiments, the first pass purification removes the early-eluting impurities. In certain embodiments, including any of the foregoing embodiments, the second pass removes the late-eluting impurities. In certain embodiments, including any of the foregoing embodiments, the purification conditions for the second, third, fourth, etc. passes are the same as for the first pass. In certain embodiments, including any of the foregoing embodiments, the purification conditions for the second, third, fourth, etc. passes are different than the first pass.

In some embodiments, including any of the foregoing embodiments, the feed stream and the raffinate stream are protected from exposure to sunlight and oxygen. In some embodiments, including any of the foregoing embodiments, the feed stream of the first and/or second pass and the raffinate stream resulting from the first and/or second pass are protected from exposure to sunlight and oxygen.

In some embodiments, including any of the foregoing embodiments, the raffinate collected after the first pass is concentrated before using as the feed stream in a second pass. In some embodiments, including any of the foregoing embodiments, the raffinate collected after the first pass is contacted with a silica plug before using as the feed stream in a second pass. In some embodiments, including any of the foregoing embodiments, the raffinate collected after the first pass is contacted with a silica plug and the effluent collected and concentrated before using as the feed stream in a second pass. In some embodiments, including any of the foregoing embodiments, the feed stream and the raffinate stream are protected from exposure to sunlight and oxygen during the concentration step(s).

In certain embodiments, including any of the foregoing embodiments, composition from the raffinate comprises substantially pure tocotrienol. In particular embodiments, the tocotrienol (i.e. alpha, beta, delta, or gamma) is at least about 80 wt % pure, at least about 85 wt % pure, at least about 90 wt % pure, at least about 91 wt % pure, at least about 92 wt % pure, at least about 93 wt % pure, at least about 94 wt % pure, or at least about 95 wt % pure, as a single isomer. In certain embodiments, including any of the foregoing embodiments, composition from the raffinate comprises substantially pure alpha-tocotrienol. In particular embodiments, the alpha-tocotrienol is at least about 80% pure, at least about 85 wt % pure, at least about 90 wt % pure, at least about 91 wt % pure, at least about 92 wt % pure, at least about 93 wt % pure, at least about 94 wt % pure, or at least about 95 wt % pure, as a single isomer. In certain embodiments, including any of the foregoing embodiments, the weight percent is a measure of the tocotrienol content versus all other impurities, including all other tocotrienols. In certain embodiments, including any of the foregoing embodiments, the weight percent is a measure of the alpha-tocotrienol content versus all other impurities. In certain embodiments, including any of the foregoing embodiments, the weight percent is measured as a UPLC response at 210 nm compared to a pure alpha-tocotrienol standard.

In certain embodiments, including any of the foregoing embodiments, composition from the raffinate comprises substantially pure tocotrienol. In particular embodiments, the tocotrienol (i.e. alpha, beta, delta, or gamma) is at least about 80 (A) % pure, at least about 85 (A) % pure, at least about 90 (A) % pure, at least about 91 (A) % pure, at least about 92 (A) % pure, at least about 93 (A) % pure, at least about 94 (A) % pure, or at least about 95 (A) % pure, as a single isomer. In certain embodiments, including any of the foregoing embodiments, composition from the raffinate comprises substantially pure alpha-tocotrienol. In particular embodiments, the alpha-tocotrienol is at least about 80% pure, at least about 85 (A) % pure, at least about 90 (A) % pure, at least about 91 (A) % pure, at least about 92 (A) % pure, at least about 93 (A) % pure, at least about 94 (A) % pure, or at least about 95 (A) % pure, as a single isomer. In certain embodiments, including any of the foregoing embodiments, the area percent is measured as a UPLC response at 210 nm. In certain embodiments, including any of the foregoing embodiments, the area percent is a measure of the tocotrienol content versus all other impurities visible at 210 nm, including all other tocotrienols. In certain embodiments, including any of the foregoing embodiments, the area percent is a measure of the alpha-tocotrienol content versus all other impurities visible at 210 nm.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: AT3 (alpha-tocotrienol); g (grams); mg (milligrams); mL (milliliters); µL (microliters); mM (millimolar); µM (micromolar); Hz (Hertz); MHz (megahertz); mmol (millimoles); h, hr or hrs (hours); min (minutes); MS (mass spectrometry); ESI (electrospray ionization); TLC (thin layer chromatography); HPLC (high performance liquid chromatography); UPLC (ultra-high performance liquid chromatography); $CDCl_3$ (deuterated chloroform); DMSO-$d_6$ (deuterated dimethylsulfoxide); MeOH (methanol); wt % (weight percent); A % or (A) % (area percent); and RVE (rotary evaporator).

For all of the following examples, standard work-up and purification methods known to those skilled in the art can be utilized. Unless otherwise indicated, all temperatures are expressed in ° C. (degrees Centigrade). All reactions are conducted at room temperature unless otherwise noted. Synthetic methodologies illustrated herein are intended to exemplify the applicable chemistry through the use of specific examples and are not indicative of the scope of the disclosure.

Non-limiting exemplary methods are described in the Examples. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

While the Examples illustrate certain of the diverse methods available for use in producing the alpha-tocotrienol compositions, they are not intended to define the scope of reactions or reaction sequences that are useful in preparing the compositions herein.

Example 1. Preparation of Alpha-Tocotrienol Enriched Compositions from Tocomin®

1. Introduction

Alpha-tocotrienol (AT3) was obtained by the chemical processing of refined palm oil (brand name Tocomin 50®). Tocomin 50® is a 50 wt % mixture of tocotrienols and tocopherols (~12% alpha-tocotrienol; ~28% combined beta-, gamma-, and delta-tocotrienol; and ~11% alpha-tocopherol). The remaining mass is thought to be made up of various esters, free acids, carotenoids, squalene, and sterols; the ratio of these impurities can vary from lot to lot. Phytosterol content of the Tocomin 50® in this example was 13.1%.

Briefly, the chemical steps consisted of a Mannich aminomethylation using 2-methylpiperazine and formaldehyde, followed by a reduction of the resultant amino functionality by use of sodium cyanoborohydride. The reaction mixture was then subjected to a series of workup steps prior to passing through a silica plug. The general synthetic scheme is shown below in Scheme 1.

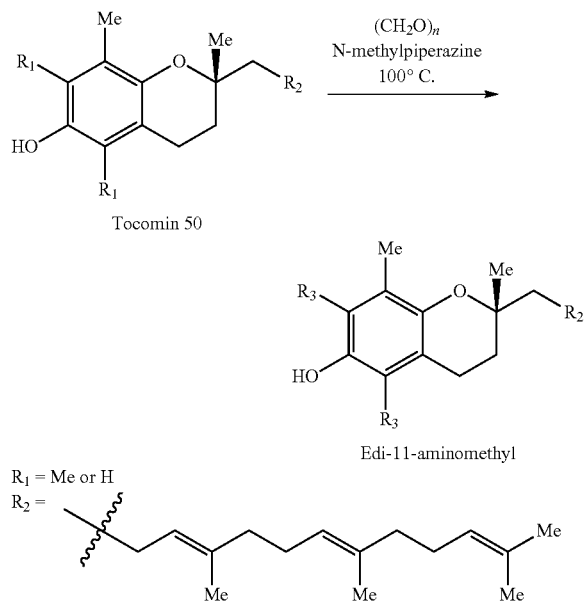

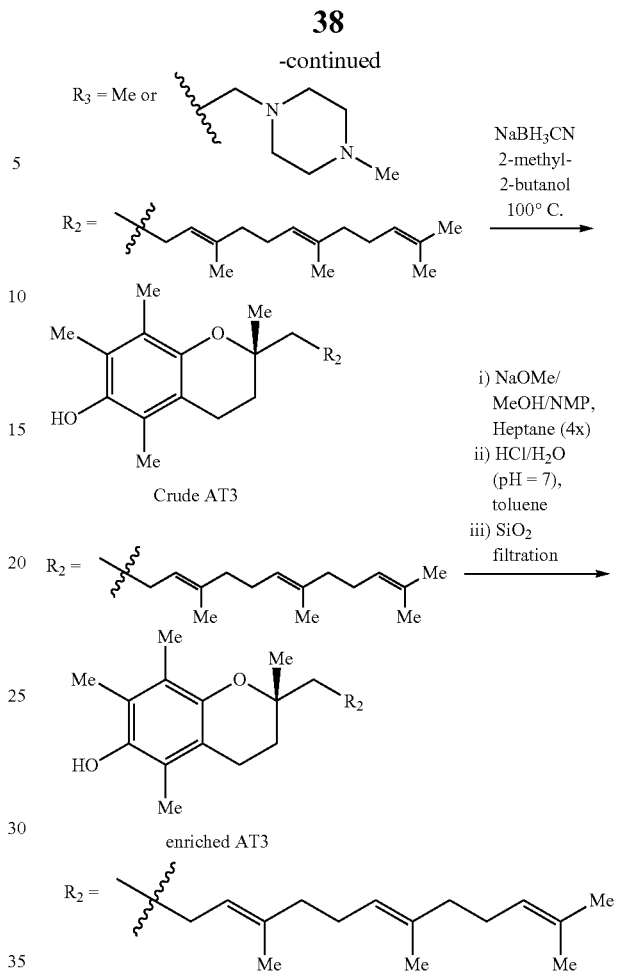

2. Procedure

A 12 L round bottom flask (reactor 1) equipped with mechanical stirrer, temperature probe, reflux condenser, and nitrogen inlet was charged with N-methyl-piperazine (0.996 kg, 9.94 mol) and paraformaldehyde (0.188 kg, 6.26 mol). The mixture was heated to 75° C. and stirred for 1.25 h (note: strong exotherm was observed at 55° C.). Tocomin 50® (2.00 kg, 2.44 mol) was charged to the flask followed by heating to 105° C. and stirring for 18 h. The reaction was cooled to 75° C. followed by addition of 2-methyl-2-butanol (3.78 kg).

A 50 L jacketed cylindrical reactor (reactor 2) equipped with a mechanical stirrer, temperature probe, nitrogen inlet, reflux condenser, and caustic scrubber was charged with 2-methyl-2-butanol (3.00 kg) and sodium cyanoborohydride (0.784 kg, 12.48 mol). This mixture was heated to 75° C. and stirred for 1 hour. The contents of reactor 1 were transferred to reactor 2 over 30 minutes. The contents were heated to 105° C. and stirred 28 hours. In process HPLC analysis showed consumption of the starting material and the contents were cooled to 22° C. Isopropyl acetate (4.26 kg) and water (2.00 kg) were charged to the reactor followed by 10% $Na_2HPO_4$ (2.00 kg). The biphasic mixture was stirred for 30 minutes and the resulting solids were filtered. The mixture was then settled for 30 minutes followed by draining the bottom aqueous layer to waste. A second wash of 10% $Na_2HPO_4$ (2.00 kg) was charged and the contents were stirred for 30 minutes followed by 30 minutes of settling. The bottom aqueous layer was drained to waste. A wash of 10% citric acid (2.50 kg) was charged and the contents were stirred for 30 minutes followed by 30 minutes of settling. The bottom aqueous layer was drained to waste.

The reflux condenser was replaced with a distillation head and condenser. The jacket temperature was set to 75° C. and vacuum was applied. The mixture was distilled to one volume (10 L). Methanol (4.00 kg) was charged and the mixture was distilled to 5 L followed by the charged of methanol (3.00 kg) and distillation to minimum stir volume. The mixture was cooled to −15° C. and Celite® (1.00 kg) was charged. This slurry was filtered and the cake was washed with methanol (2.00 kg). The filtrate was returned to reactor 2 (now warmed to 20° C.), diluted with N-methylpyrrolidone (4.00 kg), and basified with 30% NaOMe in methanol (2.64 kg). This solution was extracted once with 6.00 kg n-heptane and three times with 3.00 kg n-heptane. The n-heptane layers were discarded. The jacket was set to 10° C. and the basic methanol mixture was acidified to pH 4 with 2M HCl (7.50 kg) while maintaining a temperature below 25° C. Toluene (8.00 kg) was charged, the mixture was stirred 30 minutes followed by 30 minutes of settle time. The bottom aqueous layer was discarded. The toluene layer was washed three times with 10% brine (4.00 kg); the brine layers were discarded.

The jacket was set to 75° C. and the solution was distilled to one volume under vacuum. The solution was diluted with toluene (5 L). A bench-top filter was charged with silica gel (4.00 kg and packed in toluene). The AT3 solution was passed through the column and 9.00 kg of toluene was eluted and collected as a series of fractions. The fractions were analyzed for weight percent AT3 and all fractions (#1-11) over 50 wt % AT3 were combined. Weight percent AT3 analysis of the silica plug fractions is shown in Table 3.

TABLE 3

Weight percent AT3 analysis of the silica plug fractions.

| Fraction Number | Weight percent AT3 |
|---|---|
| 1 | 52% |
| 2 | 53% |
| 3 | 54% |
| 4 | 75% |
| 5 | 53% |
| 6 | 50% |
| 7 | 54% |
| 8 | 55% |
| 9 | 54% |
| 10 | 54% |
| 11 | 50% |
| 12 | 37% |
| 13 | 39% |

The combined fractions were then charged to a clean 30 L reactor equipped with mechanical stirrer, temperature probe, distillation head and condenser. The solution was distilled under vacuum to 25% volume (75° C. jacket temperature). Methanol (8.00 kg) was charged and the solution was distilled to 25% volume (50° C. jacket temperature). This was repeated three times. In process residual solvent GC showed 0.35% toluene content. A portion of the resulting MeOH solution was concentrated and the resulting oil was analyzed by UPLC at 52 wt %, 68 A % AT3. The extrapolated total mass of feed oil was 577 g, corresponding to 300 g total AT3 content.

3. Results and Discussion 3.1 Overview

The enrichment process described in section 2 was developed in order to enrich the AT3 content of the Tocomin 50® and remove non-visible impurities. The process sought to overcome the shortcomings of the existing processes.

3.2 Purity of AT3 Throughout the Process Steps

The AT3 content of the oil was tracked throughout the process in Table 4. The primary purity analytics being tracked were the UPLC area percent AT3, the weight percent AT3 of the crude oil, and the delta (area percent minus weight percent). The area percent AT3 represented the UPLC purity of the feed stream. This measurement accounted for only the impurities that were visible by UPLC at 210 nm. The weight percent was measured as a UPLC response at 210 nm against a pure AT3 standard (Fluka, # BCBN1012V). This was a measure of the actual AT3 content in the feed stream versus all other impurities. The delta percentage was a measure of the non-detectable impurity content in the feed material.

TABLE 4

Tracking AT3 content of the oil throughout the process.

| Process Stage | Wt % AT3 | HPLC A % AT3 | Δ% (A % − Wt %) |
|---|---|---|---|
| Mannich 18 h | — | 20.7 | — |
| Reduction 24 h | — | 56.5 | — |
| Post MeOH filtration | 23.8 | 55.8 | 32.0 |
| Tol Post NaOMe treatment | 30.8 | 57.7 | 26.9 |
| Final Enriched Product | 52.0 | 68.3 | 16.3 |

After the Mannich and reduction chemical steps, the area percent AT3 increased from 21 A % to 57 A % AT3 by converting the beta-, delta-, and gamma-tocotrienol isomers to the desired alpha-isomer. A 7% enhancement in weight percent was obtained after the basic MeOH treatment, followed by a further 21% improvement from the silica plug to give the final enriched product.

3.3 Impurity Tracking

It has been previously observed that during the reduction step, there is some regeneration of the unwanted beta-, delta-, and gamma-tocotrienol isomers. These side products are suspected to arise via a mechanism related to a reverse-Mannich reaction. The level of these 'isomers' are shown in Table 5.

TABLE 5

Tracking the combined β-, δ-, and γ-tocotrienol isomers[1] through the process.

| Process Stage | % isomers | Isomer/AT3 % |
|---|---|---|
| Mannich 18 h | 0.9 | 4.3 |
| Reduction 19 h | 8.3 | 15.0 |
| Reduction 21 h | 7.7 | 13.8 |
| Reduction 24 h | 8.4 | 14.9 |
| Final Enriched Product | 9.7 | 14.3 |

[1]The term 'isomers' refers to area of the peaks eluting immediately prior to the AT3 in the UPLC chromatogram between RRT 0.94 and 0.99. It is suspected that a significant portion of these peaks may not be beta-, delta-, or gamma-tocotrienol.
Two metrics were used to quantify the amount of these impurities. The first was the overall area percent of the combined impurities relative to the overall chromatogram. The second was the 'isomer/AT3' percentage, which is a ratio of the area counts of the impurities versus the AT3 area counts.

Example 2. SMB Purification

Provided herein is an SMB purification of alpha-tocotrienol from a feed stream prepared from Tocomin 50® according to the Example 1.

The chromatography mobile phase was methanol and the stationary phase was Fuji Chromatorex hydrophobic end-capped C18 in 20 μm diameter spherical particles. The first phase of the SMB purification was tuned to remove any compounds eluting later than alpha tocotrienol. The primary identified late-eluting impurity compound was α-tocopherol. The late-eluting impurities were isolated in the extract stream of the SMB apparatus, while the alpha tocotrienol and early-eluting impurities were isolated in the raffinate stream of the SMB apparatus.

Feed for the SMB was prepared by diluting the concentrated oil from Example 1 in methanol. The total amount of oil (577 g of alpha tocotrienol and impurities) was used to calculate the amount of methanol to dilute the supplied feed. The feed was diluted to 38 g/L.

The SMB chromatography system was equipped with 8 individual chromatography columns each 1 cm in diameter and 10 cm in length, all packed with Fuji Chromatorex C18 hydrophobic end capped 20 μm diameter stationary phase. One cycle through the eight columns was denoted as a complete cycle. The SMB throughput was 1.39 kg oil/kg stationary phase/24 hr at 21 bar or 2.32 kg oil/kg stationary phase/24 hr at 35 bar.

The raffinate stream was collected as pooled samples and analyzed for area percent alpha tocotrienol, weight percent alpha tocotrienol, and isomer content. Over 16 hourly samples, the area percent alpha tocotrienol varied from 77.7% to 82%, and the weight percent alpha tocotrienol varied from 72.1% to 76.7%. The distribution of alpha tocotrienol was 99.9% in the raffinate, 0.06% in the extract, and 0.04% in the recycle. After two passes of SMB purification, raffinate with greater than 85 (A) % purity alpha tocotrienol can be obtained.

Example 3. Preparation of Alpha-Tocotrienol Enriched Compositions from Gold Tri.E™ 70

1. Introduction

Alpha-tocotrienol (AT3) was obtained by the chemical processing of refined palm oil (brand name Sime Darby Gold Tri.E™ 70). Gold Tri.E™ 70 is a 70% mixture of tocotrienols and tocopherols. The remaining mass is thought to be made up of various esters, free acids, carotenoids, squalene, and sterols; the ratio of these impurities can vary from lot to lot.

Briefly, the chemical steps consisted of a Mannich aminomethylation using 2-methylpiperazine and formaldehyde, followed by a reduction of the resultant amino functionality by use of sodium cyanoborohydride. The reaction mixture was then subjected to a series of workup steps prior to passing through a silica plug. The general synthetic scheme is shown below in Scheme 2.

Scheme 2: Synthetic route

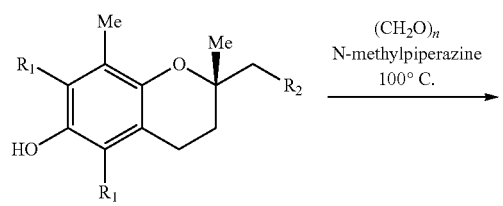

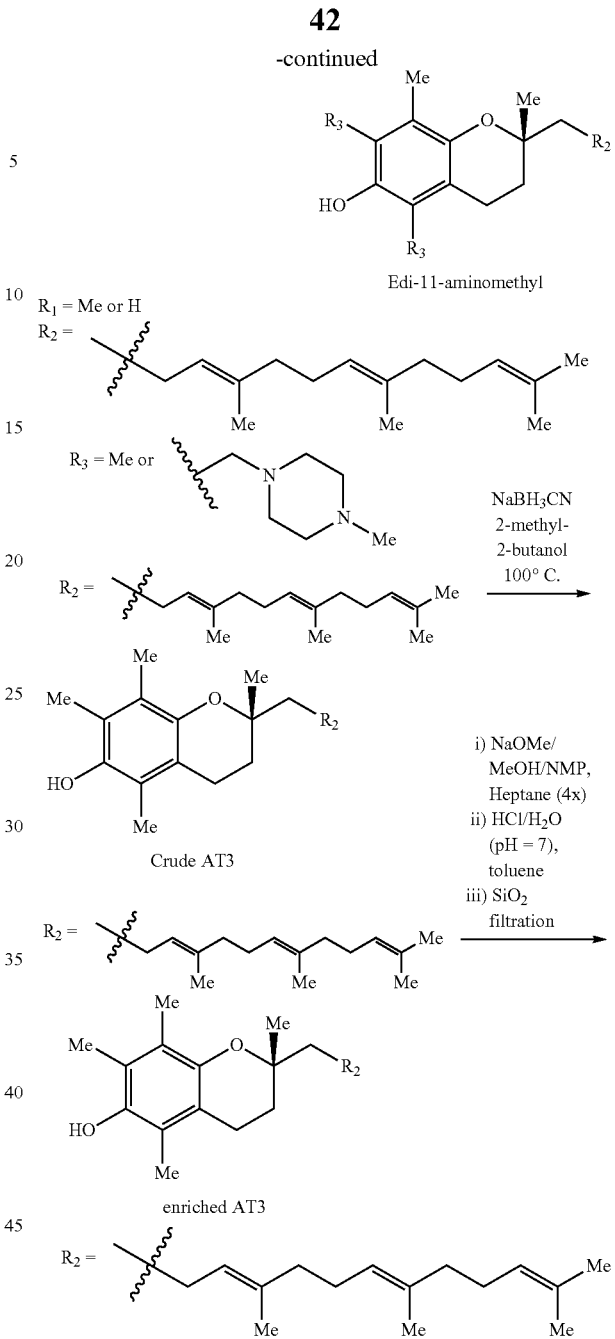

2. Procedure

A 1 L jacketed reactor (reactor 1) equipped with mechanical stirrer, temperature probe, reflux condenser, and nitrogen inlet was charged with Gold Tri.E™ 70 (400.0 g, 0.68 mol) and paraformaldehyde (52.4 g, 1.74 mol, 2.56 eq.). N-methyl-piperazine (276.0 g, 2.76 mol, 4.04 eq.) was charged slowly over 30 minutes in order to control the exotherm <27° C. internal temperature. The mixture was warmed to 75° C. and stirred for 30 minutes before warming to 105° C. and stirring for 20 h, after which time all starting material was consumed by UPLC. The reaction was cooled to 75° C. followed by addition of 2-methyl-2-butanol (520.0 g, 5.90 mol, 8.65 eq.).

A 5 L jacketed reactor (reactor 2) equipped with a mechanical stirrer, temperature probe, nitrogen inlet, reflux condenser, and caustic scrubber was charged with 2-methyl- 2-butanol (840.0 g, 9.53 mol, 13.98 eq.) and sodium cyanoborohydride (220.0 g, 3.50 mol, 5.13 eq.). Reactor 2 was heated to 75° C. and stirred for 1 hour. The contents of reactor 1 were transferred to reactor 2 over 30 minutes. The contents of reactor 2 were heated to 107° C. and stirred 28 hours, after which time in-process UPLC analysis showed consumption of the starting material and the contents were cooled to 20° C. Water (400.0 g) was charged and a mild exotherm was observed (+6° C.). iPrOAc (852.0 g) was charged and the mixture was warmed to 60° C. for 1 h in order to dissolve the majority of precipitated solids. The layers were settled for 30 minutes and the bottom aqueous phase was drained (aq: 616 g, org: 3.9 L). A second portion of $H_2O$ was charged (400 g) and the mixture was stirred at 60° C. for 30 min. then settled for 30 min. The bottom aqueous phase was drained (aq: 460 g, org: 3.6 L). The reaction mixture was cooled to 20° C. and a 30 wt % solution of citric acid/$H_2O$ (480 g, 0.75 mol, 1.10 eq.) was charged. The mixture was stirred 30 min. then settled for 30 min., after which time the aqueous phase was drained (aq: 658 g, org: 3.3 L). Reactor 2 was set to distillation mode and the jacket was set to 70° C. The volatile components were removed by vacuum distillation until the mixture became a thick oil. MeOH (600 g) was charged and then distilled until the mixture became a thick oil. The reactor was cooled to 20° C., whereupon MeOH (800 g) and celite (200 g) were charged and the slurry was cooled to −15° C. The mixture was stirred for 1 h at −15° C. and the precipitate was removed by filtration, followed by a cake wash with −15° C. MeOH (400 g).

The filtrate was returned to reactor 2, cooled to 0° C., diluted with N-methyl-pyrrolidone (800 g), and basified with 30% NaOMe in methanol (528 g) (mild exotherm +9° C.). To this solution was charged n-heptane (800 g) at 0° C. (total volume: 4.1 L), stirred 30 min, settled 1 h. The top heptane phase was removed (hept: 425 mL, MeOH: 3.7 L) and a second portion of n-heptane (600 g) was charged at 0° C. (total volume: 4.5 L), stirred 30 min, settled 30 min, and the heptane phase was removed (hept: 940 mL, MeOH: 3.5 L). The extraction with n-heptane was repeated two more times, discarding the heptane phase each time. The organic MeOH phase was returned to reactor 1 at 0° C. and the basic methanol mixture was acidified to pH 7 with 2M HCl (1510 g) while maintaining a temperature below 25° C. The jacket temperature was adjusted to 20° C., and toluene (1600 g) was charged and the mixture was stirred 30 minutes followed by 1 h of settle time. The bottom aqueous layer was discarded. The toluene layer was warmed to 60° C. and 5% brine was added. The mixture was stirred 30 min and settled 12 h in order to achieve a clean phase split. The brine phase was discarded and a second portion of 5% brine was charged (800 g) at 60° C. The phases were stirred for 30 min and then settled 12 h, at which time a clean phase split was achieved and the brine phase was discarded.

The organic phase was returned to reactor 1 (total volume 3.05 L) and the jacket was set to 75° C. The solution was distilled under reduced pressure to the desired volume (1.8 L). The toluene solution was loaded onto a silica column (800 g $SiO_2$, packed in toluene) and the light yellow eluent (560 g) was discarded. The column was and washed with toluene (2500 g) and the eluent was collected after 350 g toluene had eluted. A total mass of 2128 g eluent were collected and concentrated to a viscous orange oil. The oil was blown dry under a stream of nitrogen. A total of 180.99 g oil was collected, with 66.5 A % and 59.3 wt % AT3 by UPLC analysis. Once corrected for weight percent, a total of 107.33 g AT3 was isolated, resulting in a 49.97% theoretical AT3 yield (based of the 53.7 wt % tocotrienol content of the starting material). The material was used as the feed in for the 2-pass SMB purification.

Example 4. Waste Stream Analysis All waste streams generated during the bulk feed preparation in Example 3 were isolated and analyzed for AT3 content (AFC-704-051). The goal of this analysis was to determine if any processing steps resulted in large losses of AT3. The results of this analysis are tabulated in the form of AT3 mass (grams) and AT3 loss as a percentage of theoretical AT3 yield (Table 6). The mass balance data indicates that the processing steps are quite efficient, resulting in a total of 3.3 g lost to waste streams, or 1.65% AT3 yield loss.

TABLE 6

AT3 losses to waste streams throughout process

| Step | AT3 mass (g) | Yield lost (%) |
| --- | --- | --- |
| Aqueous quench #1 | 0.02 | 0.01 |
| Aqueous quench #2 | 0 | 0 |
| Citric acid wash | 0 | 0 |
| Hept extract #1 | 0.07 | 0.04 |
| Hept extract #2 | 0.23 | 0.11 |
| Hept extract #3 | 0.46 | 0.23 |
| Hept extract #4 | 0.25 | 0.12 |
| Neutralized aq layer | 0.14 | 0.07 |
| Brine wash #1 | 0.31 | 0.15 |
| Brine wash #2 | 0 | 0 |
| Column wash | 1.83 | 0.92 |
| Total losses | 3.30 | 1.65 |

3. Results and Discussion
3.1 Overview

The enrichment process described in section 2 was developed in order to enrich the AT3 content of the Gold Tr.E™ 70 and remove non-visible impurities. The process sought to overcome the shortcomings of the existing processes.

Example 5. SMB Purification

Provided herein is an SMB purification of alpha-tocotrienol from a feed stream prepared from Gold Tr.E™ 70 according to Example 3. The starting alpha-tocotrienol purity was 66.5 area percent and 59.3 weight percent.

The chromatography mobile phase was acetonitrile and the stationary phase was Mitsubishi MCI gel CHP20/P20 20 µm diameter particles. The first phase of the SMB purification was tuned to remove any compounds eluting later than alpha-tocotrienol. The primary identified late-eluting compound was α-tocopherol. The late-eluting impurities were isolated in the extract stream of the SMB apparatus, while the alpha-tocotrienol and early-eluting impurities were isolated in the raffinate stream of the SMB apparatus.

Feed for the SMB was prepared by diluting the concentrated oil from Example 3 in acetonitrile. The oil (167.44 g of alpha-tocotrienol and impurities) was diluted to approx. 150 g/L in acetonitrile, respectively.

The SMB chromatography system was equipped with 6 individual chromatography columns each 1 cm in diameter and 10 cm in length. One cycle through the six columns was denoted as a complete cycle. For the first pass, the SMB throughput was 0.24 kg oil/kg stationary phase/24 hr at approx. 36 to approx. 40 bar. The raffinate was collected, and 47 g alpha-tocotrienol was collected with a purity of 90.8 area percent.

The feed for the second pass was prepared by concentrating the recovered raffinate down to the desired volume.

Prior to the final evaporation, the mass of oil was estimated based on the gravimetrically determined concentration of oil in the raffinate from the first pass. A total of 47.91 g of oil was concentrated to 130 g/L. After the second pass of SMB purification at a throughput of 0.08 kg oil/kg stationary phase/24 hr, the raffinate was collected. 28.8 g alpha-tocotrienol was recovered with a purity of 90.8 area percent.

Example 6. Preparation of Alpha-Tocotrienol Enriched Compositions from Natural Palm Oil (TC84, Davos Life Science)

1. Introduction

Alpha-tocotrienol (AT3) was obtained by the chemical processing of natural palm oil (brand name Davos Life Science TC84). TC84 contains 84 A % of a mixture of tocotrienols and tocopherols, including AT3, beta-, gamma-, and delta-tocotrienol and the corresponding tocopherols. The remaining mass is thought to be made up of various esters, free acids, carotenoids, squalene, and sterols; the ratio of these impurities can vary from lot to lot.

Briefly, the chemical steps comprise a two-step telescopic process to convert beta-, gamma-, and delta-tocotrienol to AT3. Step 1 includes a Mannich reaction conducted under neat condition, followed by azeotropic distillation to remove water byproduct. The intermediates produced in Step 1 are then subjected to reductive cleavage using sodium cyanoborohydride in Step 2. The resulting enriched AT3 crude is partially purified by a plug flow silica gel filtration. Final purification is performed with an SMB chromatography separation process described in Example 7. The general synthetic scheme is shown below in Scheme 3.

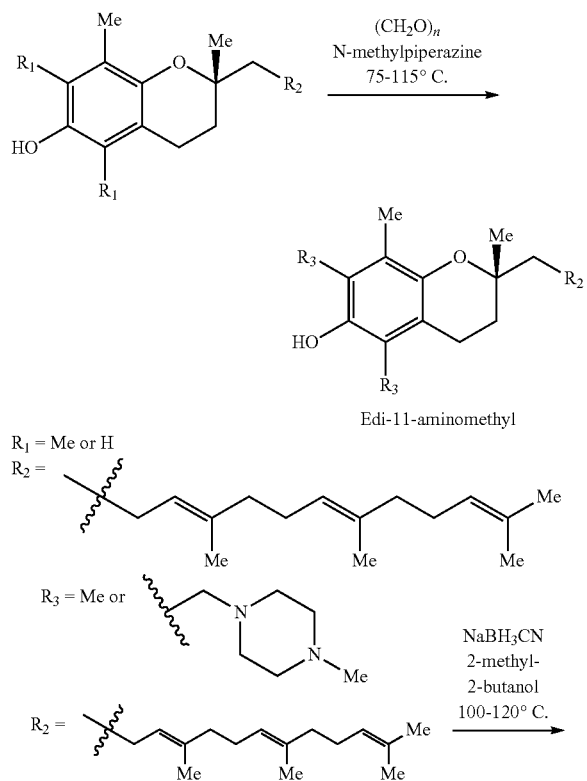

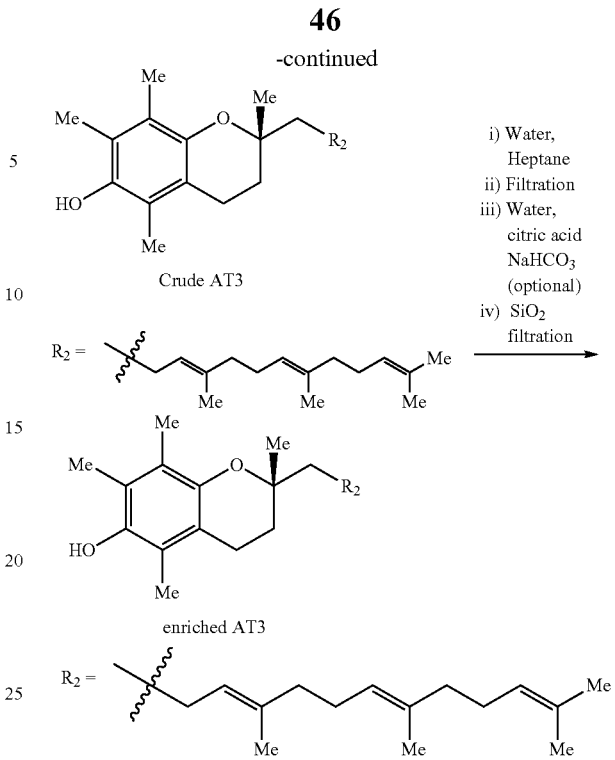

2. Procedure

Overview. The first step in the enrichment process is the Mannich reaction, which converts the beta-, gamma- and delta-tocotrienols to the mono-methyl-(N-methylpiperazinyl) intermediate in about 2-3 hours, at batch temperature of about 75° C. to 80° C. under neat condition using paraformaldehyde and N-methylpiperazine. A second Mannich reaction converts delta-tocotrienol mono-methyl-(N-methylpiperazinyl) to the the bis-methyl-(N-methylpiperazinyl) intermediate. This second Mannich reaction takes place at a batch temperature of about 110° C. to 120° C. and for a duration of about 12-16 hours. The first Mannich reaction can be completed, with or without the removal of water, in about 2-3 hours. However, since the batch temperature is limited by the refluxing temperature of the solvent (t-AmOH, about 90-104° C.), it is prevented from reaching a temperature of about 110-120° C. for the second Mannich reaction to convert. Therefore, in the presence of solvent such as t-AmOH (bp=105° C.), water is azeotropically removed during formation of Mannich reaction products. Accordingly, the Mannich reaction is performed under neat conditions in two steps: (1) the first Mannich reaction is carried out at 75-80° C. in about 2-3 hours, and (2) the second Mannich reaction is carried out at 110-115° C. in about 10-16 hours. The water by-product produced during the Mannich reaction is removed by azeotropic distillation in the presence of t-AmOH prior to the reduction reaction. Partial removal of amino compounds (e.g., N-methylpiperazine) can also occur during azeotropic distillation.

Mannich reaction. Paraformaldehyde was charged to a 10 L reactor (reactor 1) with jacket temperature set at 35° C. Warm TC84 (760 g, about 40-45° C.) was poured into the reactor from the aluminum container, followed by N-methylpiperazine. The batch was held at about 75-80° C. (jacket temperature=80° C.) for 3 hours. The jacket temperature was subsequently set to 120° C., and the Mannich reaction was complete after 20 hours with no trace of delta-/beta-/gamma-tocotrienol detected. The level of delta-tocotrienol-methyl (methylpiperazine) was less than 5 A % (about 1.3 A %). Two azeotropic distillations, under vacuum at 75-100° C., were performed with t-AmOH; the final Mannich product solution in t-AmOH has a Karl Fischer titration value (KF) of 9.2 ppm.

Reduction. In a second reactor (reactor 2), 418 g of NaCN(BH$_3$) was heated at about 75-80° C. for 1 hour in t-AmOH (1596 g) before the distillate containing the Mannich product in t-AmOH was charged. The jacket temperature was set at 115° C., allowing the batch internal temperature to reach about 104° C. At 26 hours, liquid and white solids were observed outside the vessel, collecting around one stopper, indicating the possibility of insufficient condenser cooling. An additional 248 g of NaCN(BH$_3$) was charged from a new container, and the reaction was continued for 16 hours until analysis indicated that reduction was complete (i.e., no trace of intermediate tocotrienol-Mannich product observed). However, it is possible to carry out the reduction reaction without additional charging of NaCN(BH$_3$). Accordingly, in some embodiments, the Mannich product (in t-AmOH) and NaCN(BH$_3$) are mixed and held at a temperature of about 110-115° C. for about 12-24 hours in order for the reduction reaction to proceed to completion.

Quench and wash. After completion of the reduction reaction, the batch was cooled to 20-25° C. and quenched with water (about 2S, or twice the amount of starting material), followed by addition of heptane (about 1S-2S, where S denotes a weight equivalent of starting material). The quenched batch was held for two hours at 20-25° C., and insoluble solids were filtered out. The solids were rinsed with heptane and t-AmOH, and the filtrate from each filtration step was combined and charged back to a clean reactor and allowed to phase separate. The lower aqueous phase was drained, and a water wash of the remaining organic phase was carried out. The lower aqueous phase was again drained, and aqueous citric acid (10%, w/w) was used to wash the remaining organic phase. The lower aqueous phase was drained, leaving an organic phase with a pH of about 6.5. The organic phase was then distilled with t-AmOH:heptane in a 1:99 volumetric ratio to a desired volume (about 2 L) in heptane.

Silica filtration. The heptane solution (temperature about 30-35° C.) was loaded onto a silica column (380 g SiO$_2$, 12 cm diameter×7.6 cm height) at room temperature and allowed to drain until the column was dry. The column was rinsed with 600 mL heptane from a heptane reactor rinse and combined with the eluate, making up the first column fraction. Three subsequent fractions were subsequently collected from the column, with the first two fractions containing 1.5 L of t-AmOH:heptane in a 1:99 volumetric ratio and the last fraction containing 1.5 L of 100% t-AmOH. The content of each fraction was estimated. Fraction 1 contained 65.9 A % of AT3 (about 640 g of crude AT3), and Fraction 2 contained 68.3 A % AT3 (about 14 g of crude AT3). Table 5 illustrates the contents of each fraction collected from the SiO$_2$ column.

TABLE 7

SiO$_2$ filtration fractions

| Fraction | Description | Bulk weight | Estimated content | Mass vs. starting material (760 g) | AT3 content (UPLC) |
|---|---|---|---|---|---|
| Feed | Concentrated solution before SiO$_2$ separation | N/A | | | 57.9 A % |
| 1 | 2 L batch + 0.6 L heptane rinse | 1860 g | 639.8 g | 0.84 S | 65.9 A % |
| 2 | 1.5 L heptane:t-AmOH (99:1) | 856 g | 13.6 g | 0.02 S | 68.3 A % |
| 3 | 1.5 L heptane:t-AmOH (99:1) | 878 g | 8.2 g | 0.01 S | 63.0 A % |
| 4 | 1.5 L heptane:t-AmOH (99:1) | 868.4 g | 19.6 g | N/A | 18.2 A % |
| 5 | 1.5 L t-AmOH | 1015.7 g | 99.5 g | N/A | N/D |

Fractions 1 and 2 were combined, and the fractions were distilled to reduce the volume to about 2V, followed by distillation with acetonitrile to provide a concentrated solution in acetonitrile. The final material was a suspension in acetonitrile with an oil concentration of about 280 g/L; this material was diluted with acetonitrile to about 60 g/L and used as the feed for SMB purification in Example 7.

Example 7. SMB Purification

Provided herein is an SMB purification of alpha-tocotrienol from a feed stream prepared from natural palm oil (e.g., TC84, Davos Life Science) according to Example 6. The starting material was a suspension of alpha-tocotrienol in acetonitrile with an oil concentration of about 280 g/L.

Testing of the columns used in the SMB unit was conducted with a sample of the feed stream prepared according to Example 6. Each column was 1 cm diameter×10 cm length and packed with Mac Mod C$_{18}$ AR 15-20 micron stationary phase. The columns were each tested with three analytical injections of a diluted sample of feed using acetonitrile as a mobile phase. The average retention time of alpha-tocotrienol was 2.856 (±0.056) minutes.

The feed stream starting material suspension (280 g/L) was diluted in acetonitrile to about 60 g/L and separated using Mac Mod C$_{18}$ AR 15-20 μm stationary phase. The column configuration was 1-2-2-1. The chemically treated feed solution was subjected to two passes through the mini SMB. The first pass was used to remove the impurities that elute sooner than the AT3. Under these conditions the AT3 is recovered in the extract stream. A portion of the very late eluting non-UV visible impurities may also be reduced in this first pass; these very late eluting impurities become distributed throughout the whole column set. The second pass removes the impurities that elute later than the AT3. Under these conditions the AT3 is recovered in the raffinate.

Feed for the SMB was prepared by diluting the concentrated oil from Example 6 in acetonitrile. The oil (containing alpha-tocotrienol and impurities) was diluted to approximately 60 g/L in acetonitrile, which contained about 31 g/L AT3. This feed was held at a temperature of about 45° C. so that the components would remain in solution.

The SMB chromatography system was equipped with 6 individual chromatography columns each 1 cm in diameter and 10 cm in length. One cycle through the six columns was denoted as a complete cycle. For the first pass, the SMB throughput was 0.99 kg oil/kg stationary phase/24 hr at about 35 bar operating pressure. The extract was collected, and 27.8 g alpha-tocotrienol was collected with a purity of 67.2 area percent. This corresponded to an AT3 recovery of 95% after the first pass. Table 6 illustrates the parameters of an exemplary first pass through the SMB unit.

TABLE 6

| | | | | SMB Parameters, First Pass | | |
|---|---|---|---|---|---|---|
| Zone 1 (mL/min) | Extract (mL/min) | Feed (mL/min) | Feed concentration (g/L) | Feed concentration (g/L) (pure AT3 basis) | Period (min) | RP-UPLC AT3 purity/Extract |
| 14.63 | 8.40 | 0.170 | 60.0 | 31.0 | 1.66 | 76.9% |

For the second pass through the SMB unit, the switch time was changed in order to push the AT3 into the raffinate stream. Under these conditions, the late eluting impurities are removed in the extract stream. A productivity of 0.72 kg oil/kg stationary phase/24 hr was achieved at 35 bars operating pressure. An amount of 14.92 grams of alpha-tocotrienol was recovered with a purity of 97.2 area percent. This corresponded to an AT3 recovery of 93% after the second pass. Table 7 illustrates the parameters of an exemplary second pass through the SMB unit.

TABLE 7

| | | | SMB Parameters, Second Pass | | |
|---|---|---|---|---|---|
| Zone 1 (mL/min) | Extract (mL/min) | Feed (mL/min) | Feed concentration (g/L) (pure AT3 basis) | Period (min) | RP-UPLC AT3 purity/Extract |
| 14.63 | 8.40 | 0.170 | 31.0 | 1.9 | 97.23% |

The productivity of pure AT3 in the combined first and second passes is equivalent to 0.51 kg AT3/kg stationary phase/24 hr.

The columns in the SMB unit were cleaned with isopropanol between the first and second passes. However, this step may become optional once the condition of the feed stream is optimized to maintain the components in solution.

In addition, while removal of the early eluting impurities was performed prior to removal of late eluting impurities, the two passes can be reversed if needed. Accordingly, in some embodiments, a method of purifying a tocotrienol by SMB chromatography is provided, wherein removal of the late eluting impurities takes place during the first pass under conditions provided, e.g., in Table 6, and removal of the early eluting impurities takes place during the second pass under conditions provided, e.g., in Table 5.

All publications, patents, and patent applications cited in this specification are herein incorporated by reference as if each individual publication, patent, or patent application were specifically and individually indicated to be incorporated by reference. While the claimed subject matter has been described in terms of various embodiments, the skilled artisan will appreciate that various modifications, substitutions, omissions, and changes may be made without departing from the spirit thereof. Accordingly, it is intended that the scope of the claimed subject matter is limited solely by the scope of the following claims, including equivalents thereof.

What is claimed is:

1. A method for making an alpha-tocotrienol enriched tocol mixture, comprising:
    (a) contacting a tocol mixture with an amino-alkylating agent, wherein the tocol mixture comprises at least one non-alpha tocotrienol, at least one non-tocol, optionally alpha tocotrienol, and optionally one or more tocopherols, whereby the at least one non-alpha tocotrienol is amino-alkylated;
    (b) reducing the amino-alkylated non-alpha tocotrienols to alpha tocotrienol with a reducing agent;
    (c) removing one or more waxy impurities from the mixture;
    (d) contacting the mixture with an agent that binds one or more polar impurities; and
    (e) removing the agent that binds the one or more polar impurities.

2. A method of purifying a tocotrienol from a feed solution comprising the steps of:
    a. passing the feed solution through a chromatographic process comprising a stationary phase and a mobile phase stream, wherein said feed solution comprises the tocotrienol and one or more impurity compounds;
    b. operating the chromatographic process as a simulated moving bed (SMB) process under conditions effective to purify the tocotrienol from at least one impurity compound;
    c. collecting a stream from the SMB apparatus, wherein said stream comprises the purified tocotrienol; and
    d. optionally repeating steps a.-c.

3. The method of claim 1, further comprising after step (a):
    (a)(1) removing water formed from the reaction of step (a).

4. The method of claim 1, wherein the amino-alkylating agent in step (a) comprises a secondary amine and a formaldehyde equivalent.

5. The method of claim 4, wherein the secondary amine is N-methyl-piperazine.

6. The method of claim 1, wherein the reducing agent in step (b) is $NaBH_3CN$.

7. The method of claim 1, wherein an alcohol having a boiling point of at least about 95° C. is used as a solvent in step (b).

8. The method of claim 1, wherein steps (d) and (e) comprise adding the mixture to a column comprising the agent that binds the one or more polar impurities, and eluting the mixture off the column.

9. The method of claim 1, further comprising after step (e):
    (f) solvent exchange of the mixture to acetonitrile.

10. The method of claim 1, wherein the tocol mixture is a palm oil or a material derived from palm oil.

11. The method of claim 1, wherein the tocol mixture in step (a) comprises at least about 65 (A) % tocols.

12. The method of claim 11, wherein the tocol mixture comprises 84 (A) % of a mixture of tocotrienols and tocopherols.

13. The method of claim 1, wherein the product of the method has a content of at least about 50 wt % alpha-tocotrienol.

14. The method of claim 3 wherein step (a)(1) comprises an azeotropic distillation in the presence of a solvent with a boiling point of at least 95° C. at 1 atm pressure.

15. The method of claim 14, wherein the solvent is 2-methyl-2-butanol.

16. The method of claim 1, wherein the solvent in step (b) is 2-methyl-2-butanol.

17. The method of claim 1, wherein step (c) comprises addition of heptane and holding the mixture at a temperature of about 20° C. to 30° C.

18. The method of claim 17, wherein step (c) further comprises filtering the mixture to remove insoluble solid by-products.

19. The method of claim 1, wherein step (c) comprises an aqueous work up, wherein the aqueous work up comprises (i) contacting the mixture with water, whereby an aqueous phase is formed, and removing the aqueous phase, and (ii) performing an acid wash on the mixture.

20. The method of claim 1, wherein step (c) comprises reducing the mixture to about a minimum stir volume, wherein the mixture is reduced to a minimum stir volume by distillation in the presence of a solvent, and wherein the solvent is heptane, 2-methyl-2-butanol, or a combination thereof.

21. The method of claim 1, wherein there is no intervening step to separate components of the tocol mixture between step (a) and step (b) other than an optional step to remove water formed from the reaction of step (a).

* * * * *